US006988881B2

(12) United States Patent
Motsenbocker et al.

(10) Patent No.: US 6,988,881 B2
(45) Date of Patent: Jan. 24, 2006

(54) BALLOON FOLDING TECHNOLOGY

(75) Inventors: Tom Motsenbocker, Flagstaff, AZ (US); Edward Goff, Phoenix, AZ (US); Daniel J. Kasprzyk, Flagstaff, AZ (US)

(73) Assignee: Machine Solutions, Inc., Flagstaff, AZ (US)

( * ) Notice: Subject to any disclaimer, the term of this patent is extended or adjusted under 35 U.S.C. 154(b) by 205 days.

(21) Appl. No.: 10/107,768

(22) Filed: Mar. 26, 2002

(65) Prior Publication Data

US 2002/0163104 A1   Nov. 7, 2002

Related U.S. Application Data

(60) Provisional application No. 60/278,817, filed on Mar. 26, 2001.

(51) Int. Cl.
  *B29C 53/08*   (2006.01)
(52) U.S. Cl. ............... 425/392; 425/397; 425/402; 72/402; 29/237
(58) Field of Classification Search ........... 425/392, 425/393, 397, 403, 402; 72/402; 29/237
See application file for complete search history.

(56) References Cited

U.S. PATENT DOCUMENTS

| | | | |
|---|---|---|---|
| 1,665,915 A | 4/1928 | Ekman |
| 1,889,795 A | 12/1932 | Smith et al. |
| 2,292,421 A | 8/1942 | Wolf |
| 2,751,077 A | 6/1956 | Latin et al. |
| 2,887,222 A | 5/1959 | Latin et al. |
| 3,664,213 A | 5/1972 | Anati |
| 3,695,087 A | 10/1972 | Tuberman |
| 4,413,989 A | 11/1983 | Schjeldahl et al. |
| 4,456,000 A | 6/1984 | Schjeldahl et al. |
| 4,490,421 A | 12/1984 | Levy |

(Continued)

FOREIGN PATENT DOCUMENTS

DE   295 06 654.7   7/1995

(Continued)

*Primary Examiner*—Robert Davis
*Assistant Examiner*—Thu Khanh T. Nguyen
(74) *Attorney, Agent, or Firm*—Skinner and Associates

(57) ABSTRACT

An apparatus for folding a catheter balloon comprises a stationary base member; a rotatable drive hub which is moveable in relation to the stationary base member; and a pleating head aligned with respect to the stationary base member and to the rotatable drive hub. The pleating head includes at least three segments, each having a proximal end and an angled distal end with at least one angled side face terminating in an edge of a predetermined length. Each segment has a centerline between the proximal and distal ends, each segment having a proximal point and a distal point, and the proximal point being pivotally coupled by pins to the stationary base member and the distal point being pivotally coupled by pins to the rotatable hub member. The segments are arranged so that the segment distal ends are disposed adjacent to and a predetermined distance away from a central point and defining a central aperture with a spiral-pleat dimension having at least three channels in communication with a central aperture. Also, the segment centerlines extend therefrom toward the segment distal ends and are oriented away from the central point. The segment distal ends move closer to the central point upon rotation of the rotatable hub member in a predetermined direction, whereby the balloon is disposed around a shaft substrate, aligned in the central aperture and pleated around the shaft substrate upon rotation of the rotatable hub. A method of pleating and folding a catheter balloon is also disclosed.

2 Claims, 33 Drawing Sheets

U.S. PATENT DOCUMENTS

| | | |
|---|---|---|
| 4,578,982 A | 4/1986 | Schrock |
| 4,681,092 A | 7/1987 | Cho et al. |
| RE32,983 E | 7/1989 | Levy |
| 4,854,031 A | 8/1989 | Eisenzimmer |
| 4,906,244 A | 3/1990 | Pinchuk et al. |
| RE33,561 E | 3/1991 | Levy |
| 5,026,377 A | 6/1991 | Burton et al. |
| 5,087,394 A | 2/1992 | Keith |
| 5,108,415 A | 4/1992 | Pinchuk et al. |
| 5,156,612 A | 10/1992 | Pinchuk et al. |
| 5,163,989 A | 11/1992 | Campbell et al. |
| 5,183,085 A | 2/1993 | Timmermans |
| 5,195,350 A | 3/1993 | Aikens et al. |
| 5,209,799 A | 5/1993 | Vigil |
| 5,261,263 A | 11/1993 | Whitesell |
| 5,270,086 A | 12/1993 | Hamlin |
| 5,290,305 A | 3/1994 | Inoue |
| 5,304,340 A | 4/1994 | Downey |
| 5,334,146 A | 8/1994 | Ozasa |
| 5,350,361 A | 9/1994 | Tsukashima et al. |
| 5,358,486 A | 10/1994 | Saab |
| 5,381,686 A | 1/1995 | Thorup |
| 5,411,521 A | 5/1995 | Putnam et al. |
| 5,437,083 A | 8/1995 | Williams et al. |
| 5,509,184 A | 4/1996 | Herrero |
| 5,546,646 A | 8/1996 | Williams et al. |
| 5,591,222 A | 1/1997 | Susawa et al. |
| 5,626,604 A | 5/1997 | Cottone, Jr. |
| 5,628,754 A | 5/1997 | Shevlin et al. |
| 5,630,830 A | 5/1997 | Verbeek |
| 5,672,169 A | 9/1997 | Verbeek |
| 5,700,285 A | 12/1997 | Myers et al. |
| 5,725,519 A | 3/1998 | Penner et al. |
| 5,738,674 A | 4/1998 | Williams et al. |
| 5,746,644 A | 5/1998 | Cheetham |
| 5,746,764 A | 5/1998 | Green et al. |
| 5,749,921 A | 5/1998 | Lenker et al. |
| 5,766,057 A | 6/1998 | Maack |
| 5,766,203 A | 6/1998 | Imran et al. |
| 5,792,415 A | 8/1998 | Hijlkema |
| 5,807,520 A | 9/1998 | Wang et al. |
| 5,810,871 A | 9/1998 | Tuckey et al. |
| 5,810,873 A | 9/1998 | Morales |
| 5,836,952 A | 11/1998 | Davis et al. |
| 5,836,965 A | 11/1998 | Jendersee et al. |
| 5,860,966 A | 1/1999 | Tower |
| 5,893,852 A | 4/1999 | Morales |
| 5,893,867 A | 4/1999 | Bagaoisan et al. |
| 5,911,752 A | 6/1999 | Dustrude et al. |
| 5,931,851 A | 8/1999 | Morales |
| 5,951,540 A | 9/1999 | Verbeek |
| 5,992,000 A | 11/1999 | Humphrey et al. |
| 6,009,614 A | 1/2000 | Morales |
| 6,018,857 A | 2/2000 | Duffy et al. |
| 6,024,737 A | 2/2000 | Morales |
| 6,033,380 A * | 3/2000 | Butaric et al. ......... 604/103.07 |
| 6,051,002 A | 4/2000 | Morales |
| 6,063,092 A | 5/2000 | Shin |
| 6,063,102 A | 5/2000 | Morales |
| 6,283,743 B1 | 9/2001 | Traxler et al. |
| 6,296,655 B1 | 10/2001 | Gaudoin et al. |
| 6,360,577 B2 | 3/2002 | Austin |
| 6,568,235 B1 * | 5/2003 | Kokish ....................... 72/402 |
| 6,629,350 B2 * | 10/2003 | Motsenbocker ............ 29/283.5 |

FOREIGN PATENT DOCUMENTS

| | | |
|---|---|---|
| DE | 195 32 288 A1 | 3/1997 |
| EP | 0 630 623 A2 | 12/1994 |
| EP | 0 701 800 A1 | 3/1996 |
| EP | 0 935 952 A2 | 8/1999 |
| WO | PCT/US95/08975 | 8/1996 |
| WO | PCT/US96/19739 | 6/1997 |
| WO | PCT/US97/20136 | 5/1998 |

* cited by examiner

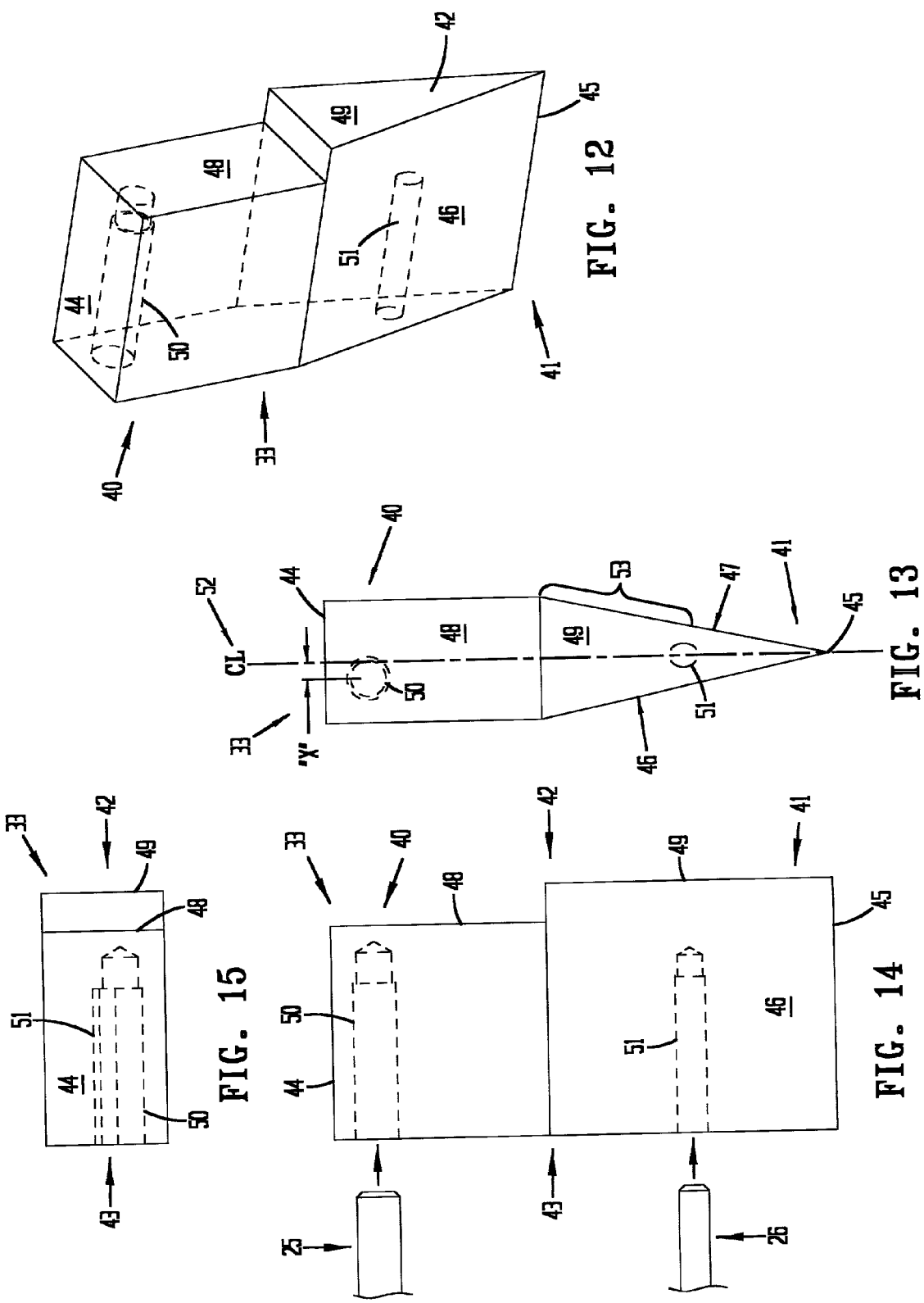

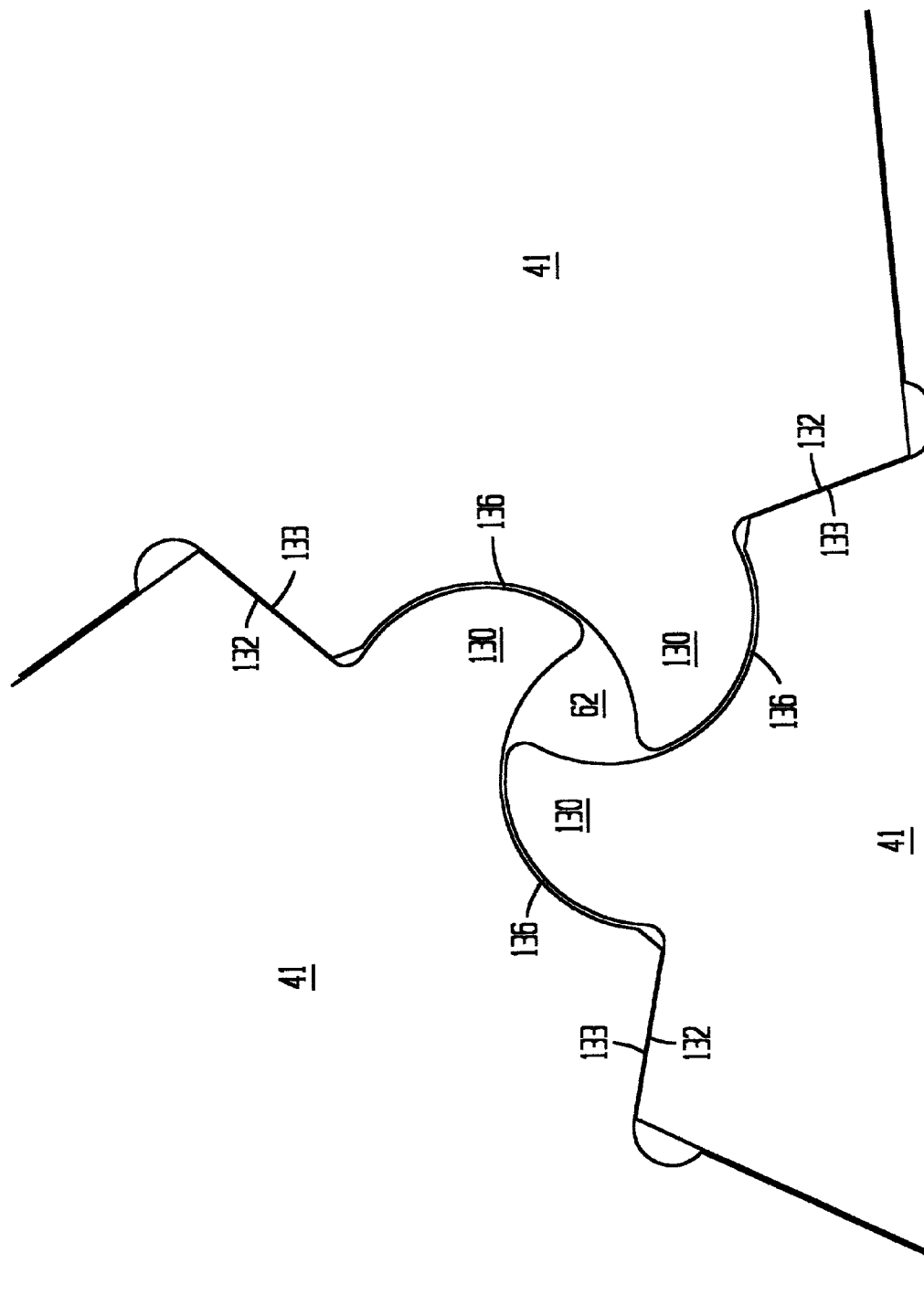

BALLOON FOLDING TECHNOLOGY

CROSS-REFERENCE TO RELATED APPLICATIONS, IF ANY

This application claims the benefit under 35 U.S.C. §119(e) of co-pending provisional application Ser. No. 60/278,817, filed Mar. 26, 2001, which is hereby incorporated by reference.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to medical devices and methods. More particularly, the invention relates to a method of making medical devices. Most particularly, it relates to a device and method for making a balloon catheter device. The balloon catheter may be used for angioplasty, stent delivery, or other interventional or diagnostic procedures.

2. Background Information

Referring to FIGS. 1 and 2, a catheter balloon 200 is relatively long and generally cylindrical when inflated. The balloon may be provided in various size, diameters and lengths. Balloon catheters are used to treat disease by being inflated in a blood vessel to improve the path for blood flow and/or to deploy a stent. The balloon is at or near the end of a long catheter shaft, which typically comprises an inner element 201 and an outer element 202, which is inserted into an appropriate blood vessel, then threaded through the circulatory system to reach the treatment site. The balloon is inflated by pressurizing it via the hollow catheter, using a pressure source outside the body. Balloons are made of a very thin but rather rigid plastic, so that the inflated diameter is predictable and doesn't vary greatly as a function of inflation pressure. Because of this, catheter balloons do not stretch like a rubber balloon when inflated, but rather they unfold.

Referring to FIG. 3, prior to inflation and during threading through the vascular system, the balloon must be folded in an orderly manner to make it as compact as possible to facilitate catheter advancement through the vascular system. The folded balloon has several approximately equal-sized lobes or "wings", which wrap in the same direction around the catheter shaft.

Balloons are folded in two steps, which are referred to herein as "pleating" and "folding".

Referring to FIG. 4, pleating is the process of dividing the circumference of the balloon into equal-sized wings or pleats 205, which, after pleating, extend radially outward from the center.

Folding is the process of wrapping the wings spirally around the catheter shaft. Folding is typically done by hand, holding the shaft in one hand while gripping and turning the adjacent part of the balloon around the catheter axis with the other hand. The balloon is folded incrementally, moving both the folding and grasping hands incrementally in steps from the proximal to the distal end of the balloon. Following the folding, the plastic balloon is typically placed in a tube or sheath to hold it in the folded position then placed at an elevated temperature for some time to set it so that it will tend to remain in the folded, lowest profile position.

Existing technology is believed to have significant limitations and shortcomings. A hand-folding process in use tends to cause a slight helix in the balloon because a torque is required to fold the wings spirally around the shaft. This torque exists between the folding hand and the grasping hand of the person folding the balloon and is evidenced by the fact that it is necessary to grasp the catheter in order to fold the balloon. Another problem with the hand-folding process is that it tends to have variable and inconsistent results. Another problem is that the manual process adds a significant labor cost to the product.

A machine folding processes attempts to fold the entire balloon at once, rather than incrementally, while grasping the catheter shaft adjacent to the balloon. The machine and process tends to be unsuccessful in folding the balloon because there is a much greater torque required to fold the entire balloon at once, and the catheter shaft, which is small in diameter and made of plastic, is unable to support the required torsion and simply deflects torsionally, or twists.

The present invention provides a folding apparatus and method which are believed to constitute an improvement over existing technology.

BRIEF SUMMARY OF THE INVENTION

The present invention provides an apparatus and method for folding a balloon.

The balloon-folding process is preferably two steps in which the first step forms the balloon into a shape with curved wings and angled wing bases (a "spiral-pleated" shape), and the second step folds the balloon tightly around the shaft by means of radial compression through diameter reduction.

The machine that accomplishes the process includes a set of pleating elements that move inward toward the balloon, leaving a gap between the elements with the desired spiral-pleat shape. A segmental folding mechanism provided by Machine Solutions, Inc. of Flagstaff, Ariz., USA, preferably accomplishes the second folding step by a radial compression step. Radial compression may be accomplished by other means such as insertion into a sheath and pulling through a tap die.

In one embodiment, the apparatus for pleating a balloon comprises:

a. at least one stationary member;

b. at least one rotatable member which is moveable in relation to the stationary member; and c. at least three segments;

i. with a proximal end and an angled distal end with at least one angled side face terminating in an edge of a predetermined length, each segment having a centerline between the proximal and distal ends, each segment having a proximal point and a distal point, one said point being pivotally coupled by pins to the stationary member and one said point being pivotally coupled by pins to the rotatable member;

ii. the segments being arranged so that the segment distal ends are disposed adjacent to and a predetermined distance away from a central point and defining a central aperture with a spiral-pleat dimension, and that the segment centerlines extending therefrom toward the segment distal ends are oriented away from the central point; and iii. the segment distal ends moving closer to the central point upon rotation of the rotatable member in a predetermined direction.

The apparatus has a first state, wherein the segment centerlines are tangentially oriented with respect to the central aperture, and a second state, wherein the segment centerlines become radially aligned with respect to the center point and the aperture closes upon rotation of the rotatable member in the predetermined direction.

At least six basic arrangements of the proximal and distal points exists:

1. The segment distal point is on the center line and coupled to the rotatable member, and the segment proximal point is disposed off the centerline and coupled to the stationary member.
2. The segment distal point is on the center line and coupled to the stationary member, and the segment proximal point is disposed off the centerline and coupled to the rotatable member.
3. The segment distal point is off the center line and coupled to the rotatable member, and the segment proximal point is disposed on the centerline and coupled to the stationary member.
4. The segment distal point is off the center line and coupled to the stationary member, and the segment proximal point is disposed on the centerline and coupled to the rotatable member.
5. The segment distal point is off the center line and coupled to the rotatable member, and the segment proximal point is disposed off the centerline and coupled to the stationary member.
6. The segment distal point is off the center line and coupled to the stationary member, and the segment proximal point is disposed off the centerline and coupled to the rotatable member.

For each of these embodiments there may be one stationary member and one rotatable member or two stationary members and two rotatable members.

The most preferred embodiment of the single stationary member, single rotatable member apparatus for pleating a balloon by segmental radial compression, comprises:

a. a stationary base member;
b. a rotatable drive hub which is moveable in relation to the stationary base member; and
c. a crimping head aligned with respect to the stationary base member and to the rotatable drive hub, and including at least three segments;
   i. the segments each having a proximal end and an angled distal end with at least one angled side face terminating in an edge of a predetermined length, each segment having a centerline between the proximal and distal ends, each segment having a proximal point and a distal point, the distal point being disposed off the centerline and the proximal point being disposed off the centerline, and the proximal point being pivotally coupled by pins to the stationary base member and the distal point being pivotally coupled by pins to the rotatable hub member;
   ii. the segments being arranged so that the segment distal ends are disposed adjacent to and a predetermined distance away from a central point and defining a central aperture with a spiral-pleat dimension with at least three channels in communication with a central aperture, and that the segment centerlines extending therefrom toward the segment distal ends are oriented away from the central point; and
   iii. the segment distal ends moving closer to the central point upon rotation of the rotatable hub member in a predetermined direction, whereby the balloon is disposed around a shaft substrate, aligned in the central aperture and pleated around the shaft substrate upon rotation of the rotatable hub.

The most preferred embodiment of the dual stationary member, dual rotatable member apparatus for pleating a balloon by segmental radial compression, comprises:

a. a pair of aligned, stationary base members separated a predetermined distance;
b. a pair of aligned rotatable drive hubs which are moveable in relation to the stationary base member and in synchronization with each other; and
c. a pleating head aligned with respect to the base members and the drive hubs, and including at least three segments;
   i. the segments each having a proximal end and an angled distal end with at least one angled side face terminating in an edge of a predetermined length, each segment having a centerline between the proximal and distal ends, each segment having a proximal point and a distal point, the distal point being disposed off the centerline and the proximal point being disposed off the centerline, and the proximal point being pivotally coupled by pins to the stationary base members and the distal point being pivotally coupled by pins to the rotatable hub members;
   ii. the segments being arranged so that the segment distal ends are disposed adjacent to and a predetermined distance away from a central point and defining a central aperture with a spiral-pleat dimension with at least three channels in communication with a central aperture, and that the segment centerlines extending therefrom toward the segment distal ends are oriented away from the central point; and
   iii. the segment distal ends moving closer to the central point upon rotation of the rotatable hub members in a predetermined direction, whereby the balloon is disposed around a shaft substrate, aligned in the central aperture and pleated around the shaft substrate upon rotation of the rotatable hub.

The invention also provides a method of pleating a balloon comprising the steps of:

a. providing an arrangement of a plurality of segments, each having a predetermined shape with a proximal end and an angled distal end, with at least one angled side face terminating in an edge of a predetermined length, each segment having a centerline between the proximal and distal ends, each segment having a proximal point and a distal point, one said point being pivotally coupled by pins to the stationary member and one said point being pivotally coupled by pins to the rotatable member, the segments being arranged so that the segment distal ends are disposed adjacent to and a predetermined distance away from a central point and defining a central aperture with a spiral-pleat dimension, and that the segment centerlines extending therefrom toward the segment distal ends are oriented away from the central point; and
b. placing a balloon on a shaft substrate;
c. inserting the balloon and shaft substrate into the central aperture; and
d. rotating the rotatable member in a predetermined direction so that the segment distal ends move closer to the central point, whereby the central aperture contacts, compresses and pleats the balloon on the shaft substrate.

The invention also provides a system for pleating and folding a balloon comprising:

A. a balloon pleating head device including:
  a. a stationary base member;
  b. a rotatable drive hub which is moveable in relation to the stationary base member; and
  c. a pleating head aligned with respect to the stationary base member and to the rotatable drive hub, and including at least three segments;
    i. the segments each having a proximal end and an angled distal end with at least one angled side face terminating in an edge of a predetermined length, each segment having a centerline between the proximal and distal ends, each segment having a proximal point and a distal point, the distal point being disposed off the centerline and the proximal point being disposed off the centerline, and the proximal point being pivotally coupled by pins to the stationary base member and the distal point being pivotally coupled by pins to the rotatable hub member;
    ii. the segments being arranged so that the segment distal ends are disposed adjacent to and a predetermined distance away from a central point and defining a central aperture with a spiral-pleat dimension having at least three channels in communication with a central aperture, and that the segment centerlines extending therefrom toward the segment distal ends are oriented away from the central point; and
    iii. the segment distal ends moving closer to the central point upon rotation of the rotatable hub member in a predetermined direction, whereby the balloon is disposed around a shaft substrate, aligned in the central aperture and pleated around the shaft substrate upon rotation of the rotatable hub; and B. a pleated balloon folding device including;
  a. a stationary base member;
  b. a rotatable drive hub which is moveable in relation to the stationary base member; and
  c. a folding head aligned with respect to the stationary base member and to the rotatable drive hub, and including at least ten segments;
    i. the segments each having a proximal end and an angled distal end with at least one angled side face terminating in an edge of a predetermined length, each segment having a centerline between the proximal and distal ends, each segment having a proximal point and a distal point, the distal point being disposed off the centerline and the proximal point being disposed off the centerline, and the proximal point being pivotally coupled by pins to the stationary base member and the distal point being pivotally coupled by pins to the rotatable hub member;
    ii. the segments being arranged so that the segment distal ends are disposed adjacent to and a predetermined distance away from a central point and defining a central aperture with a cylindrical dimension, and that the segment centerlines extending therefrom toward the segment distal ends are oriented away from the central point; and
    iii. the segment distal ends moving closer to the central point upon rotation of the rotatable hub member in a predetermined direction, whereby the pleated balloon disposed around a shaft substrate, is aligned in the central aperture and folded around the shaft substrate upon rotation of the rotatable hub.

The invention also provides a method of pleating and folding a balloon comprising the steps of:
  a. providing a first arrangement of a plurality of segments, each having a predetermined shape with a proximal end and an angled distal end with at least one angled side face terminating in an edge of a predetermined length, each segment having a centerline between the proximal and distal ends, each segment having a proximal point and a distal point, one said point being pivotally coupled by pins to the stationary member and one said point being pivotally coupled by pins to the rotatable member, the segments being arranged so that the segment distal ends are disposed adjacent to and a predetermined distance away from a central point and defining a central aperture with a spiral-pleat dimension, and that the segment centerlines extending therefrom toward the segment distal ends are oriented away from the central point;
  b. providing a second arrangement of a plurality of segments, each having a predetermined shape with a proximal end and an angled distal end with at least one angled side face terminating in an edge of a predetermined length, each segment having a centerline between the proximal and distal ends, each segment having a proximal point and a distal point, and one said point being pivotally coupled by pins to the stationary member and one said point being pivotally coupled by pins to the rotatable member, the segments being arranged so that the segment distal ends are disposed adjacent to and a predetermined distance away from a central point and defining a central aperture with a cylindrical dimension, and that the segment centerlines extending therefrom toward the segment distal ends are oriented away from the central point;
  c. placing a balloon on a shaft substrate;
  d. inserting the balloon and shaft substrate into the first arrangement central aperture;
  e. rotating the rotatable member of the first arrangement in a predetermined direction so that the segment distal ends move closer to the central point, whereby the central aperture contacts, compresses and pleats the balloon onto the shaft substrate to form a pleated balloon;
  f. rotating the rotatable member of the first arrangement in an opposite direction and removing the pleated balloon from the first arrangement;
  g. inserting the pleated balloon and shaft substrate into the second arrangement central aperture;
  h. rotating the rotatable member of the second arrangement in a predetermined direction so that the segment distal ends move closer to the central point, whereby the central aperture contacts, radially compresses and folds the pleated balloon onto the shaft substrate to form a folded balloon; and
  i. rotating the rotatable member of the second arrangement in an opposite direction for removing the folded balloon from the second arrangement.

The features, benefits and objects of this invention will become clear to those skilled in the art by reference to the following description, claims, and drawings.

BRIEF DESCRIPTION OF THE SEVERAL VIEWS OF THE DRAWING

FIG. 11B is a perspective exploded view of the balloon pleating head of FIG. 11a.

FIG. 12 is a perspective view of an individual segment of the balloon folding head, which shows certain features in phantom.

FIG. 13 is a front view of the segment of FIG. 12.

FIG. 14 is a side view of the segment.

FIG. 15 is an end view of the segment.

FIG. 30A is an enlarged cross sectional view of a pleating head, with three segments in the closed condition.

DETAILED DESCRIPTION

The balloon-folding process is preferably two steps, in which the first step forms the balloon into a shape with curved wings 210 and angled wing bases 211 (a "spiral-pleated" shape), and the second step folds the balloon tightly around the shaft by means of radial compression through diameter reduction.

The machine that accomplishes the pleating and folding process includes a set of pleating elements 212 that move inward toward the balloon, leaving a gap 213 between the elements with the desired spiral-pleat shape. A segmental folding mechanism provided by Machine Solutions, Inc. of Flagstaff, Ariz., USA, preferably, accomplishes the second (folding) step. Radial compression may be accomplished by other means, such as insertion into a sheath and pulling through a tap die.

The present invention avoids the problems of the prior art by operating on the entire balloon at once, while applying zero net torque to the balloon, thereby not requiring any adjacent grasping of the balloon or shaft to support torsion and not causing any spiraling of the balloon. The machine accomplishes the process in two steps that we shall call pleating and folding, but both the pleating and folding steps are significantly different from the prior art.

Figure 1:
FIG. 1 illustrates a common balloon catheter.
Figure 2:
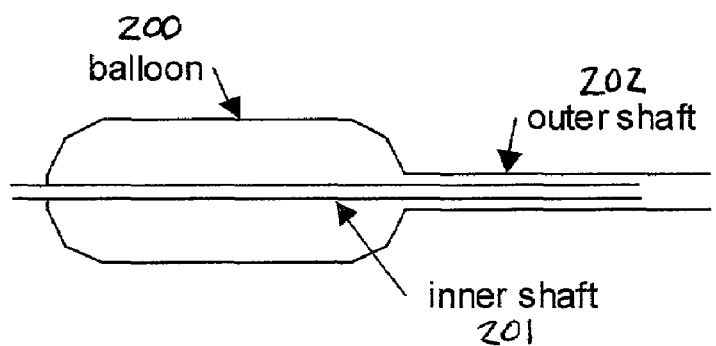
FIG. 2 illustrates a portion of a balloon catheter.
Figure 3:
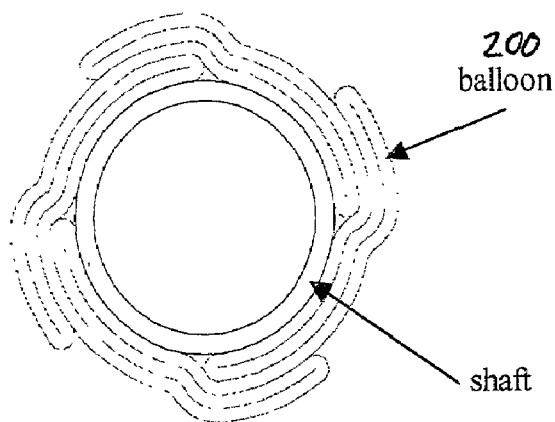
FIG. 3 illustrates a portion of a folded balloon.
Figure 4:
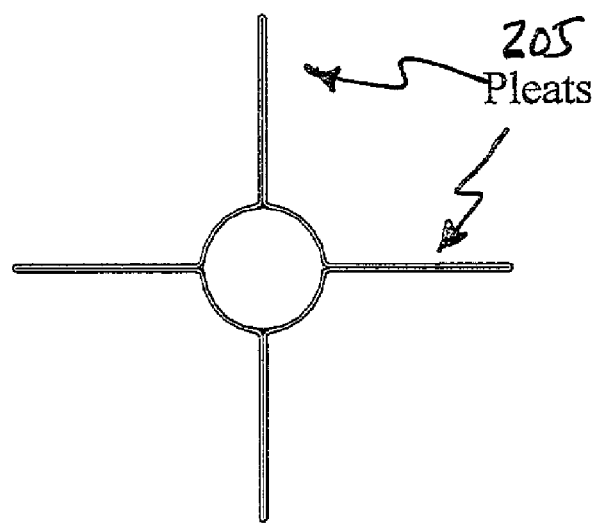
FIG. 4 illustrates a portion of a pleated balloon.
Figure 5:
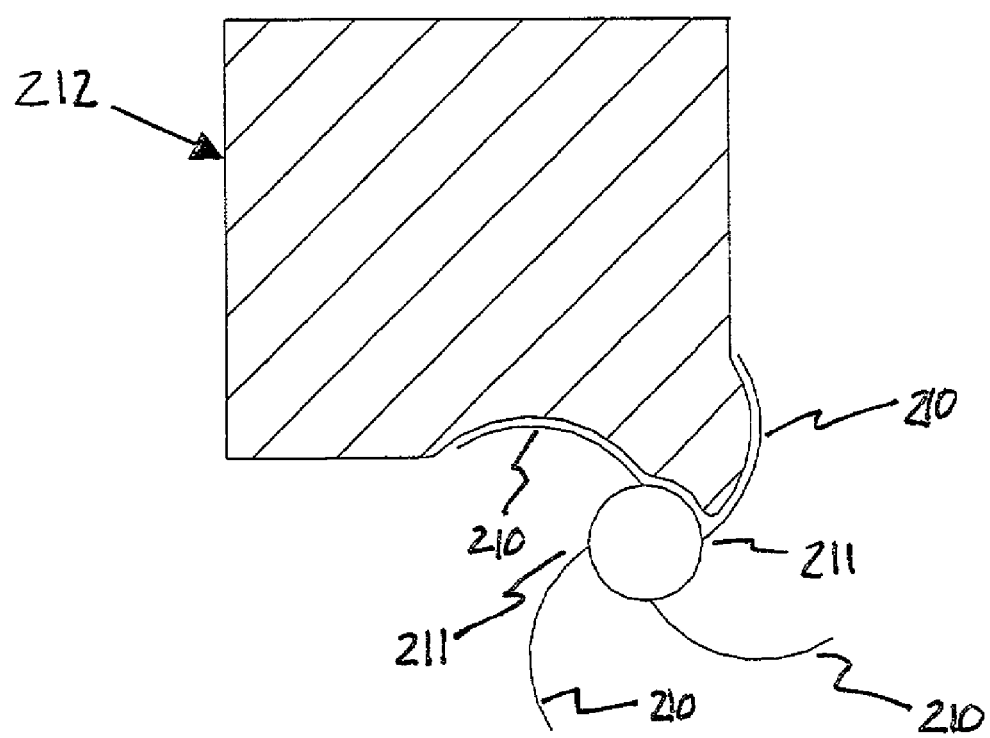
FIG. 5 illustrates a step in the balloon folding process of the present invention, utilizing the balloon pleating apparatus of the present invention.
Figure 6:
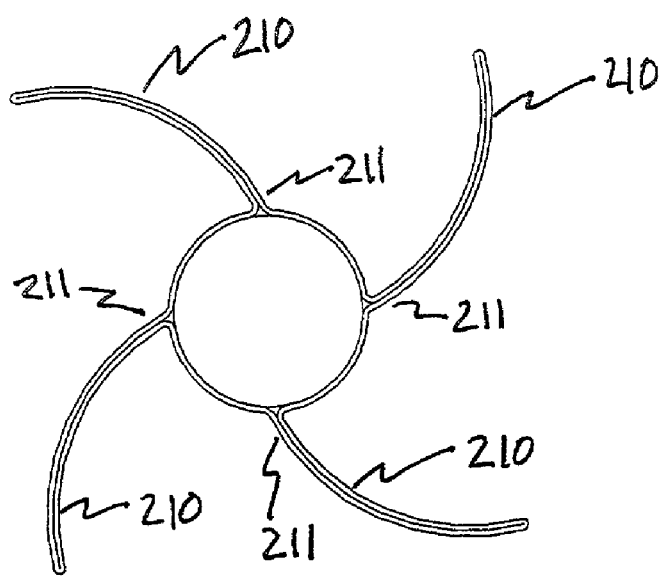
FIG. 6 illustrates a portion of a balloon pleated by the process.
Figure 7:
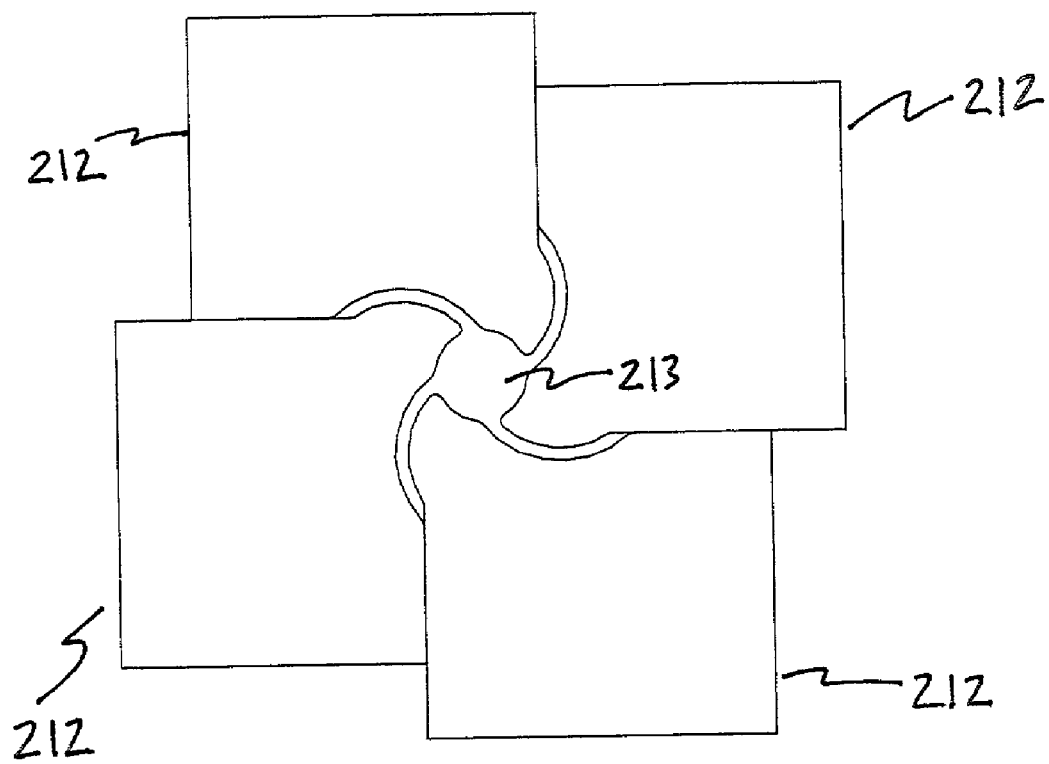
FIG. 7 illustrates a portion of the balloon pleating apparatus.

The first step is the pleating process, which is done by moving a set of identical, specially shaped elements inward to compress the lightly-inflated balloon. These elements force the balloon into a "spiral-pleat" shape, wherein the wings are curved and the base of the wings are angled and not directed radially outward. One specially shaped element contacting a balloon is shown in FIG. 5. While the elements are holding the balloon, a vacuum is typically applied to the inside of the balloon so that the balloon will retain its "spiral-pleat" shape after the elements are removed, as illustrated in FIG. 6. Four pleating elements in closed position provide a "spiral-pleat" shaped central aperture, as seen in FIG. 7. The pleating elements may be heated to impart a set to the balloon material to further induce it to retain the spiral-pleated shape after the elements are removed or when positive pressure is applied to the catheter inflation channel.

The pleating elements fill the space between the wings as the wings are being formed, thereby applying a zero net torsion to the balloon itself, so that no torsion is required to be applied externally. The spiral-pleat shaping of the pleated balloon (FIG. 6) causes it to fold predictably, in the desired way, when a subsequent radially-inward compression is applied.

The next step is the folding process, in which the spiral-pleated balloon is compressed so that the wings are held close to the catheter shaft. Because of the spiral-pleated shape, the folding is done by radial compression, where the balloon is placed in a circular, cylindrical-shaped opening that reduces its diameter, such as a shrinking tube, a funnel-shaped tube, or a segmental folding mechanism, as supplied by Machine Solutions Inc. of Flagstaff, Ariz. Following or during the compression, the balloon is typically held in the folded position, while being exposed to an elevated temperature for some period of time to impart a set to the balloon so that it will retain the folded shape after removal from the compression mechanism.

A suitable segmental folding mechanism is disclosed in U.S. Pat. No. 6,629,350 which is hereby incorporated by reference as part of the specification.

Figure 8:
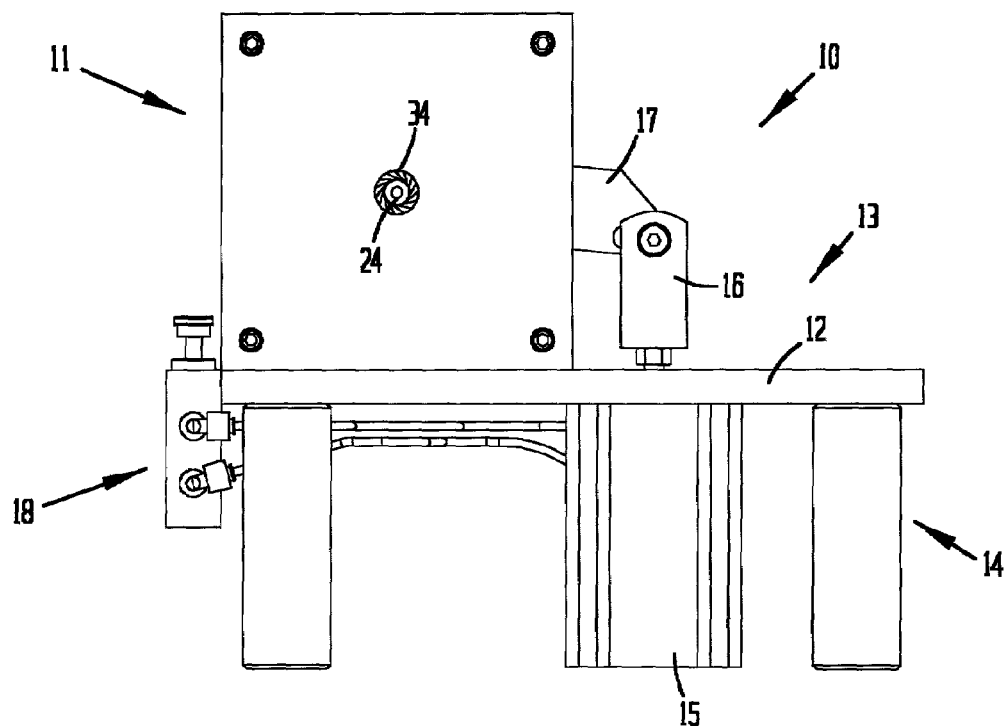
FIG. 8 is a front, plan view of a balloon pleating system of the present invention.
Figure 9:
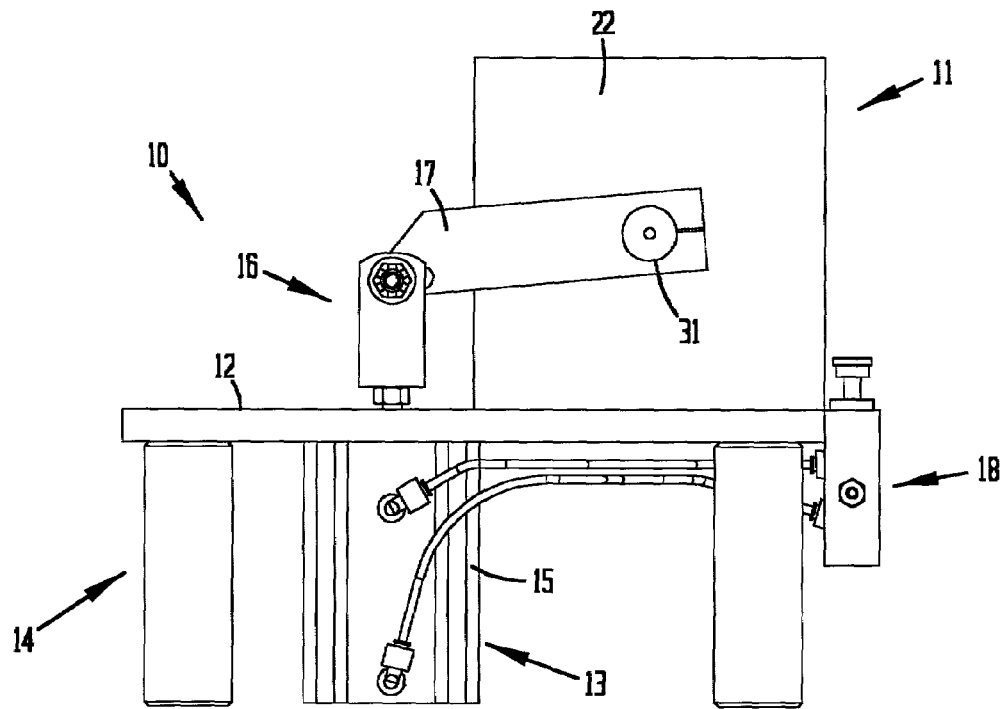
FIG. 9 is a rear or back plan view of the balloon pleating system of FIG. 8.

Referring to FIGS. 8 and 9, an embodiment of the system 10 for pleating balloons and the like generally includes a pleating head 11, a base 12, and an actuator 13. The pleating head 11 is disposed on the base surface 12 and primarily functions to accept and pleat balloons. The actuator 13 powers the pleating head. The actuator 13 preferably includes a drive mechanism 15, a linkage assembly 16 communicatively connected to the drive mechanism 15, an actuation arm 17 communicatively connected to the linkage assembly and to the pleating head 11, and an actuation control system 18 communicatively connected to the drive mechanism 15. The actuator 13 may be hand and/or foot operable by an operator. The actuator 13 is preferably a pneumatic system. Alternatively, hydraulic, mechanical, electrical, or electromechanical actuators may be used consistent with the basic teachings of the invention. The base 12 is preferably a particularized table structure having a flat work surface of a predetermined area and supported, as shown by supports or legs 14, a predetermined, optimal distance above the ground for performing the pleating function. It is within the purview of the invention that the pleating head 11 may be disposed on an existing table, bench or other work surface.

Additional systems, assemblies or mechanisms may be added to the basic system outlined above. These additional systems include, but are not limited to, handling and alignment control and/or indication devices, pressure regulation and/or indication systems, calibration systems, control devices such as mechanical stops, vision assistance, laser micrometers, vacuum evacuation systems, heating and/or cooling systems, interchangeable pleating heads, and pleating dwell timers. Further, the system 10 may be controlled by an operator or automated.

Figure 10:
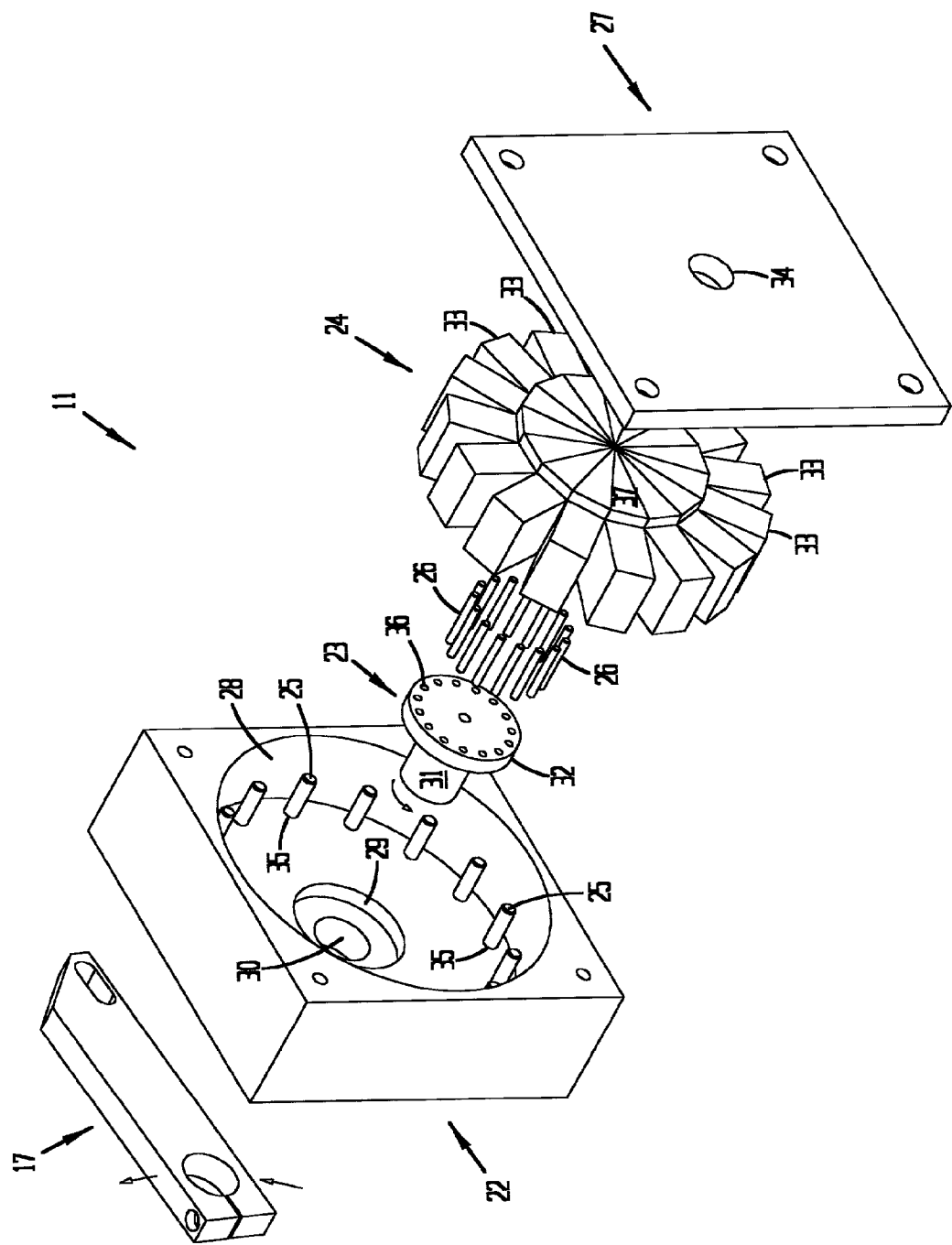
FIG. 10 is an exploded view of a pleating head, utilized in the balloon pleating system of FIGS. 8 and 9.

Referring also to FIG. 10, the pleating head 11 shown has a relatively compact, preferably rectilinear, configuration. The pleating head 11 basically comprises a base or housing 22, a drive hub 23, a radial compression wedge 24, a plurality of pivot pins 25, a plurality of drive pins 26, and a face plate or cover 27. The base 22 has a predetermined depth or thickness with a wedge chamber 28, a hub chamber 29, and a hub aperture 30. The hub 23 has a stem portion 31 and a plate portion 32. The wedge 24 consists of a plurality of separate segments 33. The cover 27 has a centrally disposed aperture 34.

The hub 23 is constructed of rigid, preferably metallic, material. The stem portion 31 of the hub 23 has a cylindrical configuration with a predetermined length and circumference, such that it extends through the hub aperture 30 of the base 22. The stem portion 31 extends a predetermined distance out of the base 22 and is connected to the actuator arm 17. In this embodiment, the actuator arm 17 moves in a counter-clockwise direction during actuation to perform a holding, compressing or pleating function. The base 22 is also constructed of a rigid, preferably metallic, material. The plate portion 32 of the hub 23 also has a cylindrical configuration with a predetermined depth and circumference, such that it is housed within the hub chamber 29 of the base 22. The hub 23 is rotatable with respect to the base 22. When the hub plate portion 32 is operatively disposed in the hub chamber 29, its front face is approximately flush with the back wall of the wedge chamber 28. The wedge 24 has a roughly cylindrical configuration with a predetermined maximum depth and circumference, such that it is housed within the wedge chamber 28 of the base 22. The cooperating depths and circumferences of the wedge 24 and wedge chamber 28, respectively, permit the wedge 24 to move within the wedge chamber 28 during a pleating operation. The pivot pins 25 are constructed of a rigid, preferably metallic, material. The pivot pins 25 are cylindrical and have a predetermined length and diameter. The pivot pins 25 are preferably disposed in cylindrical slots or bores 35 in the back wall of the wedge chamber 28 of the base 22. The pins 25 are preferably held in the slots 35 via a frictional fit. The slots 35 are disposed in a circular pattern, equally spaced apart a predetermined distance from each other and from the center of the wedge chamber 28. The drive pins 26 are constructed of a rigid, preferably metallic, material and have a cylindrical configuration with a predetermined length and diameter. The drive pins 26 mate with slots or bores 36 in the plate portion 32 of the hub 23. The drive pins 26, preferably, have a slightly smaller horizontal dimension than that of the slots 36 to permit removal of pins 26 therefrom. Each slot 36, preferably, has a cylindrical configuration which is slightly elongated along an axis extending from the center of the hub 23. The slots 36 are disposed in a circular pattern, equally spaced apart a predetermined distance from each other and from the center of the hub 23. The number of pivot pins 25 and drive pins 26 is equal to the number of segments 33 in the wedge 24, and each segment 33 is associated with and pivotally coupled to one pivot pin 25 and one drive pin 26. The pivot pins 25 and drive pins 26 mate with corresponding slots or bores in the back face of the wedge segments 33. When the wedge 24 is operatively disposed within the wedge chamber 28, the face plate 27 fits over the base 22 generally flush with a raised central portion 37 of the front face of the wedge 24 formed by the segments 33.

Figure 11A:
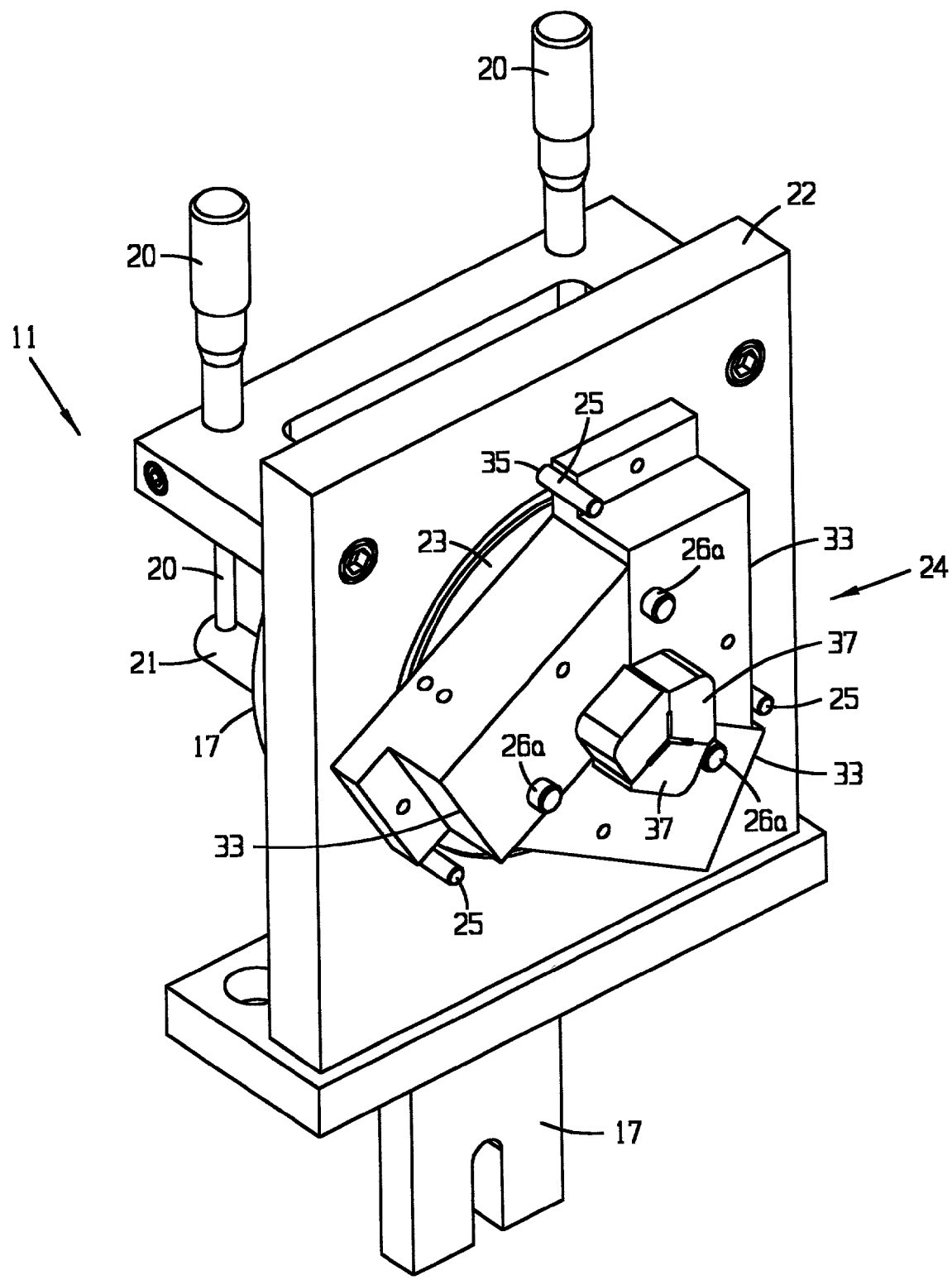
FIG. 11A is a perspective view of another embodiment of the pleating head, utilized in the balloon pleating system.
Figure 11B:
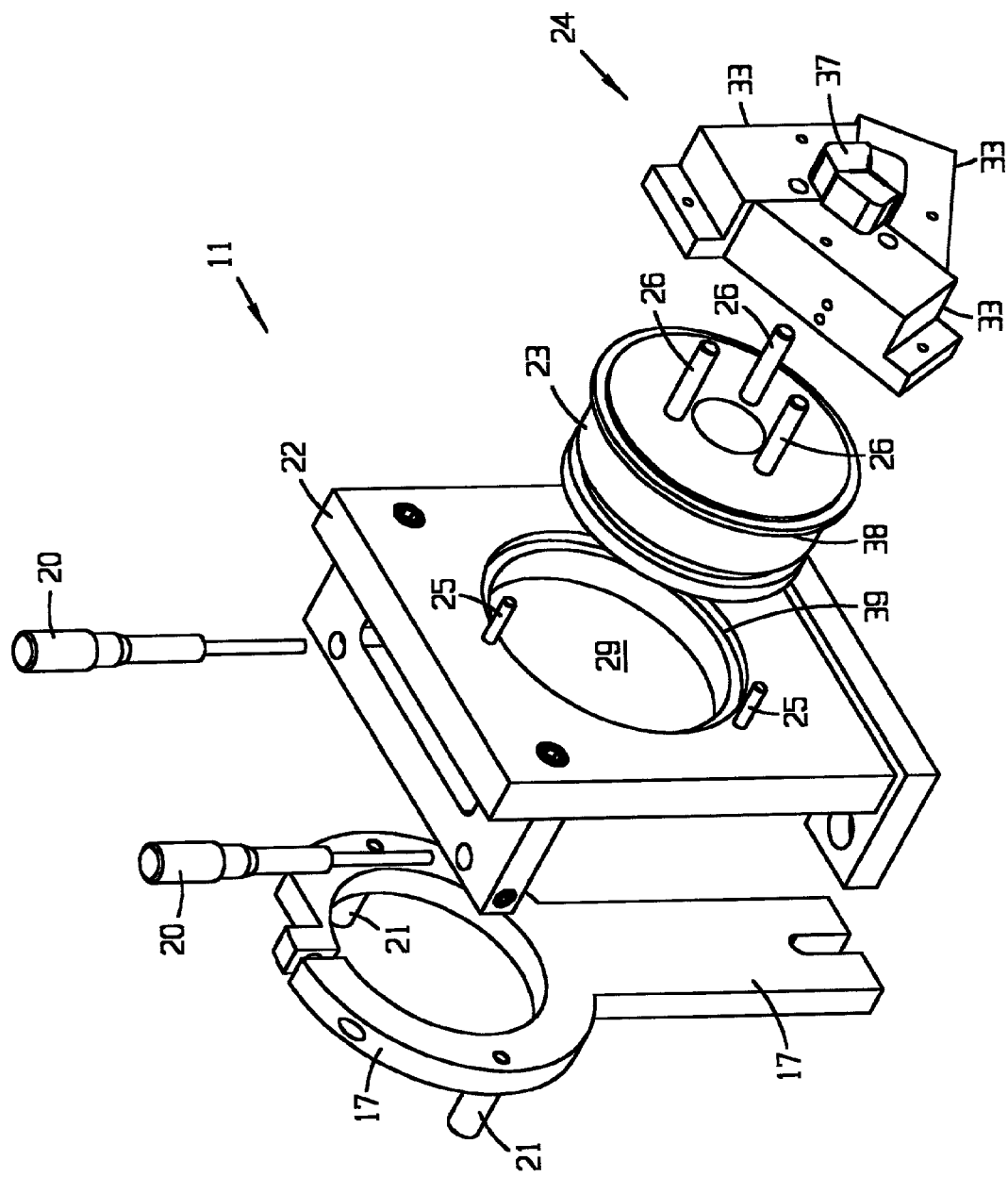

Referring now to FIGS. 11a and 11b, another embodiment of the pleating head 11 is shown without the face plate 27, for purposes of clarity. The pleating head 11 comprises a base or housing 22, a drive hub 23, a radial compression wedge 24, a plurality of pivot pins 25, a plurality of drive pins 26, and a face plate or cover 27 with central aperture 34 (not shown). The base 22 has a predetermined depth or thickness with a hub chamber 29. The hub 23 is generally cylindrical with a hub central aperture 38. The wedge 24 consists of a plurality of separate segments 33, in this embodiment a total of three.

The hub 23 is constructed of rigid, preferably metallic, material. The hub 23 has a cylindrical configuration with a predetermined length and circumference, such that it is rotatable in the hub chamber 29 of the base 22 and may ride on a bearing or bushing 39 therein. When the hub 23 is operatively disposed in the hub chamber 29 of the base 22, its front face is approximately flush with the front surface of the base 22. The hub 23 is fastened at its rear face by circumferential enclosure by the actuation arm 17 that positions and supports the hub 23 within the hub chamber 29 of the base 22. In this embodiment, the actuator arm 17 moves in a counter-clockwise direction, during actuation, to perform a holding, compressing or pleating function.

The base 22 is also constructed of a rigid, preferably metallic material, and the pivot pins 25 are constructed of a rigid, preferably metallic material. The pivot pins 25 are cylindrical and have a predetermined length and diameter. The pivot pins 25 are preferably disposed in cylindrical slots or bores 35 in the front face of the base 22. The pins 25 are preferably held in the slots 35 via a frictional fit. The slots 35 are disposed in a circular pattern, equally spaced apart a predetermined distance from each other and from the center of the hub chamber 29. The drive pins 26 are constructed of a rigid, preferably metallic, material, and have a cylindrical configuration with a predetermined length and diameter. The drive pins 26 mate with slots or bores 36 in face of the hub 23. The drive pins 26 preferably have a slightly smaller horizontal dimension than that of the slots 36 to permit removal of pins 26 therefrom. Each slot 36 preferably has a cylindrical configuration which is slightly elongated along an axis extending from the center of the hub 23. The slots 36 are disposed in a circular pattern, equally spaced apart a predetermined distance from each other and from the center of the hub 23. The drive pins 26 are operatively secured to the wedge segments 33. The number of pivot pins 25 and drive pins 26 is equal to the number of segments 33 in the wedge 24, and each wedge 24 is associated with and pivotally coupled to one pivot pin 25 and one drive pin 26. The drive pins 26 mate with corresponding slots, or bores, in the back face of the wedge segments 33 and extend there through with a fastener 19, such as a threaded nut, to rotatably secure the segment 33 to the drive pin 26. In this embodiment, the pivot pins 25 are disposed exterior the wedge segment 33, and the segment is biased against the pivot pin 25 by a biasing means, such as a spring. When the wedge 24 is operatively disposed within the base 22 and the hub 23, the face plate 27 fits over the base 22, generally flush with a raised central portion 37 of the front face of the wedge 24 formed by the segments 33. A pair of adjustable stop rods 20 is threadably secured to the base 22. Each stop rod 20 is positioned to contact a corresponding stop peg 21 fastened to the actuation arm 17. These actuation arm stops operate to limit rotational movement of the attached hub 23 and drive pins 26 to control the movement of the segments with respect to the central aperture therein.

Figure 16:
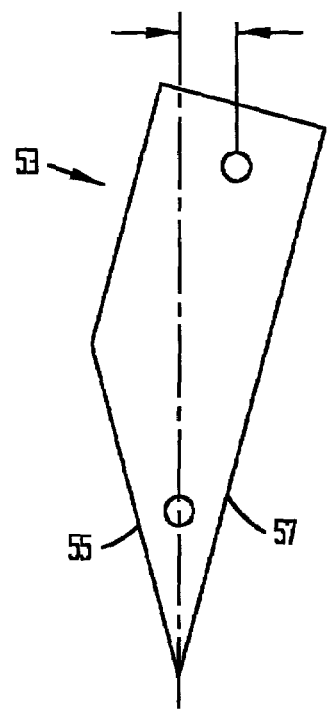
FIG. 16 illustrates an alternative embodiment of a pleating segment of the present invention with a single angle plane and a proximal offset pin aperture.
Figure 17:
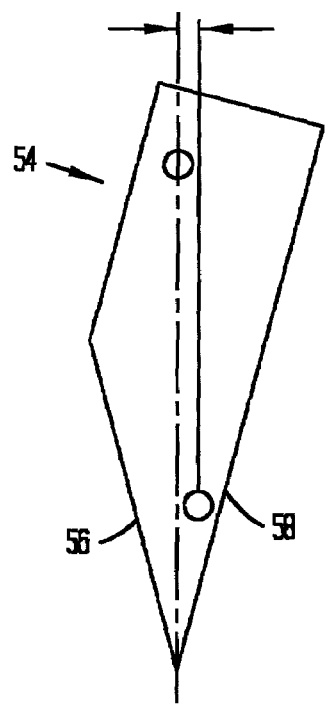
FIG. 17 illustrates an alternative embodiment of a pleating segment of the present invention with a single angle plane and a proximal offset pin aperture.

Referring to FIGS. 12–15, each segment 33 preferably has a rectilinear configuration with a proximal end 40, a distal end 41, a front face 42 and a rear face 43. A proximal end face 44 is preferably flat and rectangular with a predetermined area. The distal end 41 preferably terminates in a thin edge 45 formed at the intersection of side faces 46 and 47. Although the distal end 41 is shown to have a rectilinear, flat and uniform dimension, with particular dimensions, it may be alternatively configured with a curvilinear, non-flat, textured, and/or non-uniform surfaces, such as stepped geometries and various specialized surface textures, in a variety of dimensions. The distal end 41 can include a truncated end to provide particular gripping, compression or pleating function, depending upon the article configuration and material. The width of edge 45 is variable between approximately 5 and 100 mm and is based upon the length of the balloon to be pleated or article to be engaged, held and/or radially compressed. Preferably, both side faces 46 and 47 are angled and equivalent. FIG. 13 shows optional incut portion 53 of face 47, which face is disposed away from the wedge 24 actuation direction. This provides tip angle tolerance during disactuation of the wedge 24. FIGS. 16 and 17 show alternative segment embodiments 53 and 54, wherein respective single faces 55 and 56 are angled and opposing respective faces 57 and 58 are not angled. Returning to the preferred embodiment, front face 42 has a proximal lower portion 48 and a distally oriented raised or extended portion 49. A combination of the raised portions 49 of the faces 42 of all of the segments yields center portion 37. Center portion 37 provides optimum wedge 24 stability with minimal friction.

Rear face 43 has a proximally oriented pivot slot 50 and a distally oriented drive slot 51. The center point of the pivot slot 50 is disposed a predetermined distance, "X", away from a centerline 52 of the segment 33 which runs from the center distal point of the segment 33 (in this embodiment, edge 45) to the center proximal point. Pivot slot 50 has a predetermined vertical depth and cylindrical configuration for mating with the pivot pin 25, which is coupled to the stationary base 22. The pivot slot 50 preferably has a predetermined diameter, which is slightly greater than that of the pivot pin 25, to permit removal of the pivot pin 25 therefrom. The center point of the drive slot 51 is disposed on the centerline 52. Drive slot 51 has a predetermined vertical depth and cylindrical configuration. The drive pin 26 is preferably friction fitted into the drive slot 51. In this configuration, each drive pin 26 mates with a respective radially elongated cylindrical slot 36 of the rotatable drive hub 23. The radially elongated cylindrical slot 36 permits slight radial movement of the drive pin 26. This preferred structure provides longitudinal or radial clearance for any drive pin 26 which is not creating sufficient geometric offset in relation to an angle plane 46 or 47 of a segment 33 during actuation. An acceptable alternative arrangement is to slightly, radially elongate the segment 33, the drive slot 51, and to construct the drive hub slot 36 as a circle.

Figure 18:
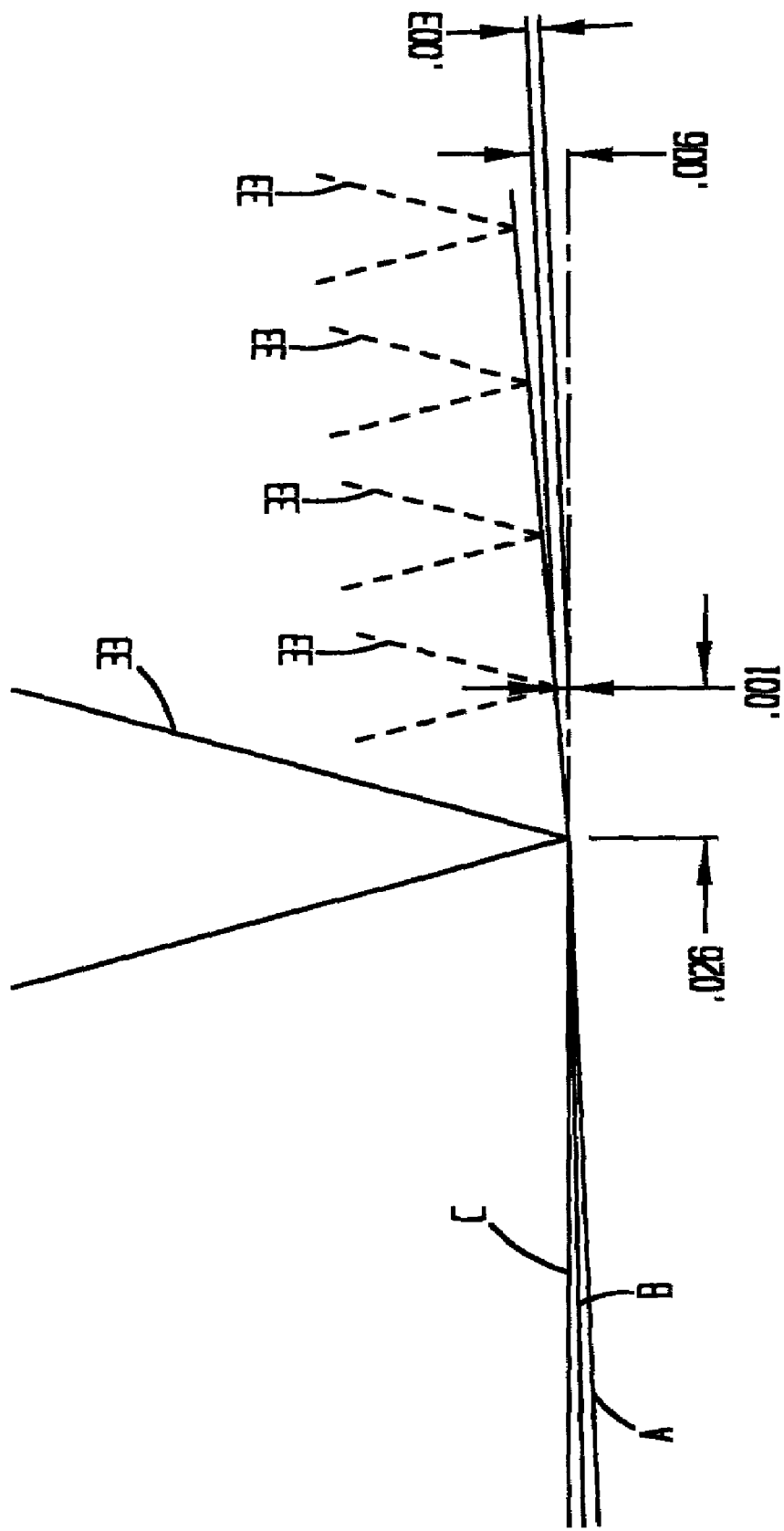
FIG. 18 is a diagram that illustrates variations in tip paths of a segment with respect to different pin offset distances from a segment centerline.
Figure 19:
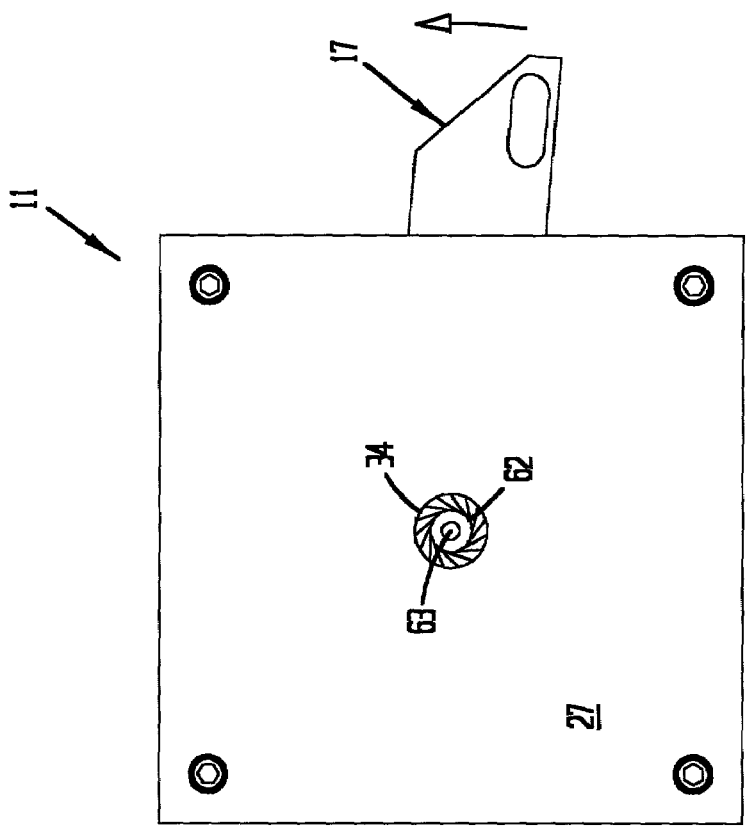
FIG. 19 is a front plan view of the balloon folding head with an access aperture in an open position.
Figure 20:
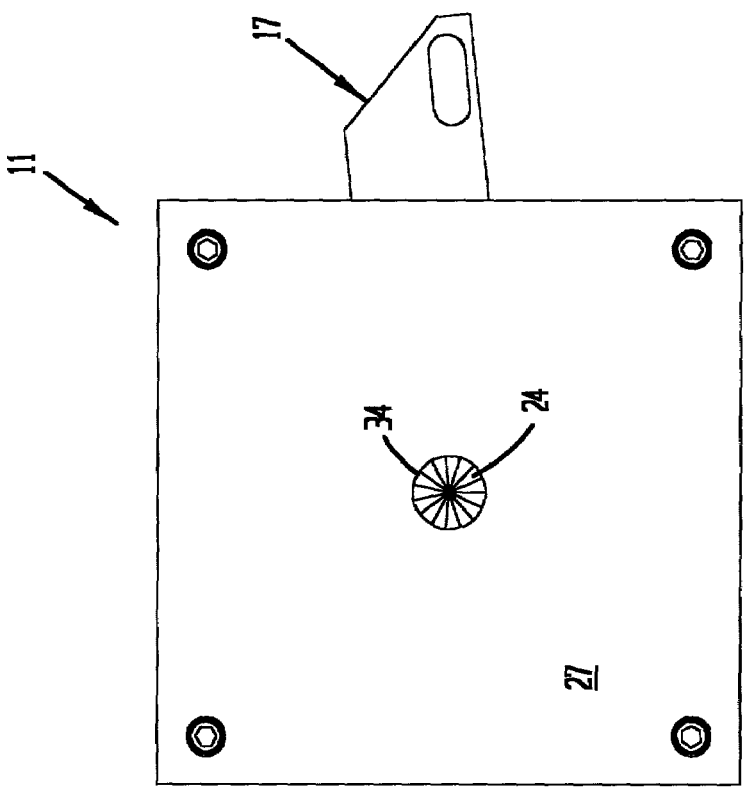
FIG. 20 is a front plan view of the balloon folding head of FIG. 19 with the access aperture in a closed position.
Figure 21:
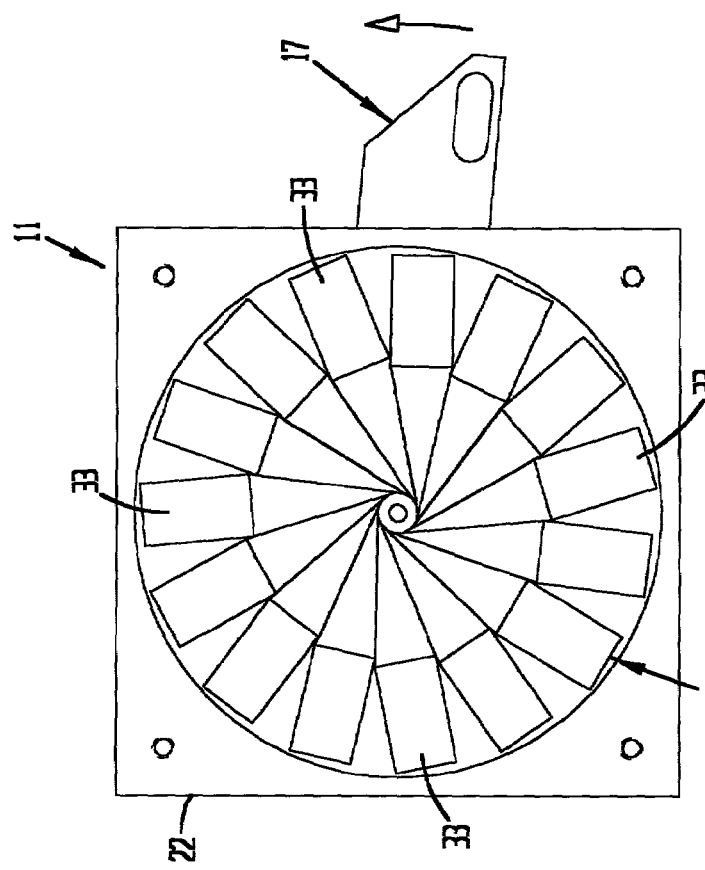
FIG. 21 is a front plan view of the balloon folding head of FIG. 19, with a face plate removed to show the position of internal segments corresponding to the open aperture of FIG. 19.
Figure 22:
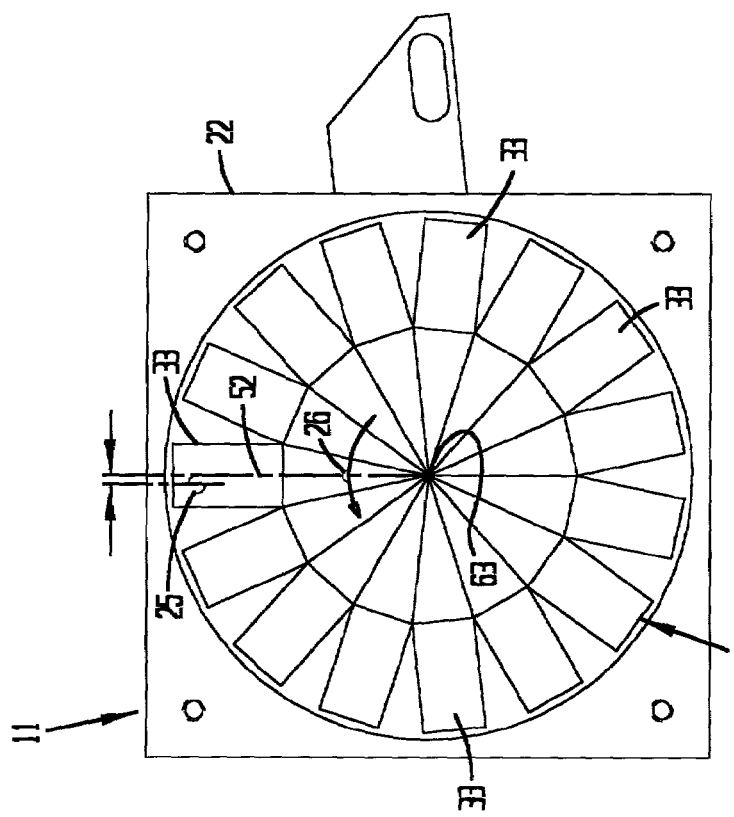
FIG. 22 is a front plan view of the balloon folding head of FIGS. 19 and 20, with the face plate removed to show the position of internal segments corresponding to the closed aperture of FIG. 20.

In general, the pin offset from the centerline provides tolerance for movement of the segments 33 through the operating range of the pleating wedge 24. This tolerance permits opening of the pleating head, the process of which is described below. The pivot pin 25 offset distance from the centerline 52 preferably ranges from 0.05 to 0.200 inches. A preferred pivot pin offset distance is 0.050 inches for medium and large diameter pleating applications. Larger offset distances provide advantages, such as reduction of tip wear and damage minimization during the pleating of small diameter balloons and other articles. Referring to FIG. 18, the increased pin offset distances from the segment centerline decreases required tolerance at the close diameter and less segment friction within the operating range of the pleating head, due to plane shifting. The tip paths of a segment with different pivot pin offsets are shown. Twenty-four degree angle planes shift back from center 0.006 at a 5 mm open position with a 0.125-inch pin offset distance. With the pin offset at 0.050 inch, the tip path line is flat in comparison to a horizontal reference line. The tolerance between segments must increase with the 0.050 inch offset distance enough to reduce internal friction and concerns of wear. Tolerance allows the tips to flex and is vulnerable to damage, particularly during use with a small article. By increasing the offset to 0.125 inches, the pleating head moves freely from a working diameter of 5 mm to 0.5 mm, without excessive internal friction, with reduced concerns of wear, with no increase of introduced shear, and with tightness in the closed position. The increased pin offset allows the angle planes to pull back more rapidly in relation to the actuation hub position. At a 0.052-inch open diameter, the exemplary tip is shifted back 0.001 inches. The advantage to having the segments interfere at the closed position is reduced tip flex, which allows the system to pleat onto a small diameter mandrel without segment damage. A 0.125 inch offset distance is preferable to 0.200 inch or higher offset distances, due to large gaps, which will occur in the open position at such offsets.

The segments 33 are preferably constructed of a polymeric material, such as Delrin or Delrin AF, polycarbonate, PEEK or Ertalyte. Alternatively, they may be constructed of a thermoplastic material, a ceramic material, a composite material, or a metallic material such as stainless steel.

The segments 33 have a preferred length from the distal to the proximal end of about 1.5 inches, a preferred width of about 0.375 inches and preferred depths or thickness of 0.625 inches minimum, and 0.750 inches maximum. The distal slot center is about 0.441 inches from the distal tip, and the proximal slot center is about 1.375 inches from the distal tip. A preferred angle for the angled faces is about twenty-four degrees.

Referring also to FIGS. 19–22, in operation, the wedge 24 has an initial, fully open state with a centrally disposed pleating aperture 62, (best shown in FIGS. 19 and 21), a fully closed state, wherein the aperture 62 has a minimum size (best shown in FIG. 20 and 22), and a plurality of intermediate states between the initial fully open state and the fully closed state, wherein the aperture 62 becomes progressively smaller. The maximum diameter of the aperture 62 is variable, up to approximately 12.0 mm. The minimum diameter is also variable, approaching zero. The length or depth of the aperture 62 is also variable between approximately 1 mm and 100 mm. A balloon to be pleated or another article to be engaged and/or radially compressed is inserted and longitudinally advanced a desired distance into the aperture 62 in the initial, open state. The balloon is pleated by rotating the actuation arm 17 counter-clockwise, which contracts the aperture 62. Contraction causes the aperture 62 wall to contact and exert a radially compressive force on the balloon. The balloon diameter is reduced a desired amount and engages a catheter body or another structure, as desired, in a balloon manufacturing process. At the desired reduced diameter, the actuator arm 17 is held in position for a desired dwell time, typically between 0 and 20 seconds. Subsequently, the actuator arm 17 is rotated clockwise to expand the aperture 62 and release engagement of the balloon. The balloon and related structure is retracted and removed from the aperture 62.

Still referring to FIGS. 19–22, the pleating aperture 62 has a substantially circular, horizontal dimension and a predetermined length, which yields a substantially cylindrical, longitudinal dimension. As the aperture 62 contracts and becomes smaller, the periphery of the aperture 62 radially moves towards the longitudinal center axis 63 of the aperture 62 in a substantially uniform manner, whereby the aperture 62 wall maintains a substantially cylindrical configuration through the closing process. Uniform compression is the result of the interaction, primarily, of the plurality of segments 33 and the pins 25 and 26, in concert with the respective base 22 and hub 23. In an open state, where aperture 62 exists, the centerlines 52 of the respective segments 33 do not radially extend out from the central axis point 63. During actuation, the centerlines 52 converge towards the central axis 63. In the fully closed state, the centerlines 52 extend radially outward from the central axis point 63. This process brings the distal portions 41 of the segments 33 closer to the center, until, ultimately the distal most portion of each segment, in this embodiment the edges 45, essentially, contact the central axis point 63. Due to the symmetry of the wedge 24 elements, each segments behaves identically, and the closure process is highly uniform.

The above mentioned segmental centerline 52 convergence process results from pivotal movement of the distal portion 41 of each segment 33 with respect to the stationary proximal portion 40 of the segments 33. The drive hub 23 rotates counter clockwise, with respect to the stationary base 22. The distal portions 41 of the segments 33 are moved or driven by the drive hub 23, which is pivotally coupled to each segment 33 by the drive pins 26, mated with slots 36 and 51. The proximal portions 40 of the segments 33 are held in a stationary position, but allowed to pivot, by the base 22, which is coupled to each segment 33 by the pivot pins 25 mated with slots 35 and 50.

Figure 23C:
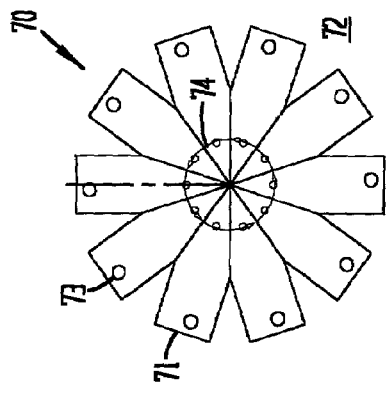
FIGS. 23A, B and C show a sequence of movement of an embodiment of the balloon pleating head, as the pleating aperture proceeds from an open to a closed state, the head embodiment having a proximal offset and being distally driven.
Figure 23B:
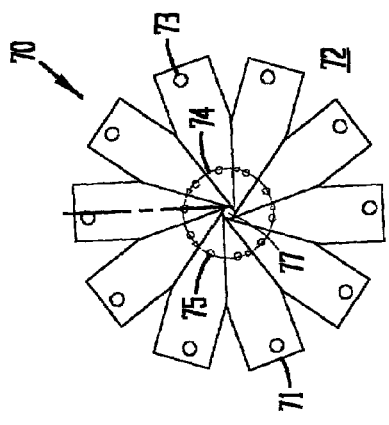
Figure 23A:
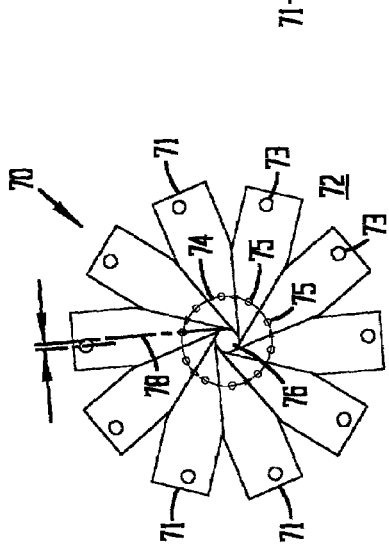

The segmental, radial compression apparatus and the process with distally driven, on-centerline drive pins and proximal, off-centerline pivot pins is further illustrated in FIGS. 23A–C. The wedge 70 is identical to the wedge 24 of the previous embodiment, except that is has ten segments 71 instead of fifteen. Proximal portions of the segments 71 are pivotally coupled to a stationary base 72 by pivot pins 73, which are disposed off centerline 78 to the left (towards the direction of drive hub 74 rotation). Distal portions of the segments 71 are coupled to a driven (counter clockwise rotatable) hub 74 by drive pins 75, which are disposed on centerline 78. The drive pins 75 are permitted a slight amount of radial movement with respect to the drive hub 74 or to the segment 71, via elongated slotting previously described. FIG. 23A illustrates a first state with fully open aperture 76. The centerlines 78 of the segments 71 are not radially aligned, and the distal most points of the segments are spaced from wedge's central axis. FIG. 23B illustrates a second, intermediate state wherein the hub 74 is traveling. The centerlines of the segments 71 are still not radially aligned. The distal most points of the segments are approaching the wedge's central axis 77. FIG. 23C illustrates a final state, where the aperture is closed. The centerlines of the segments 71 are aligned and radiate from the central axis 77. The aperture is fully closed.

Figure 24C:
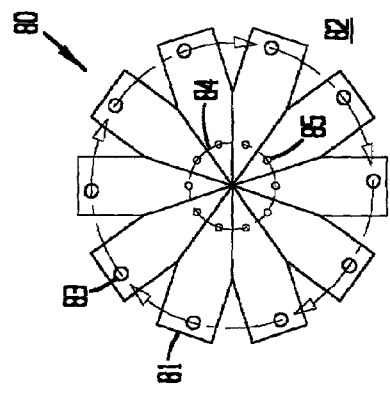
FIGS. 24A, B and C show a sequence of movement of an alternative embodiment of the balloon pleating head, as the pleating aperture proceeds from an open to a closed state, the head embodiment having a proximal offset and being proximally driven.
Figure 24B:
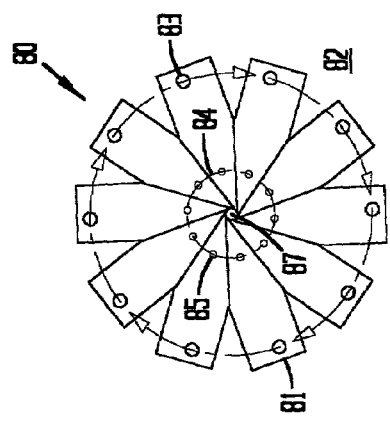
Figure 24A:
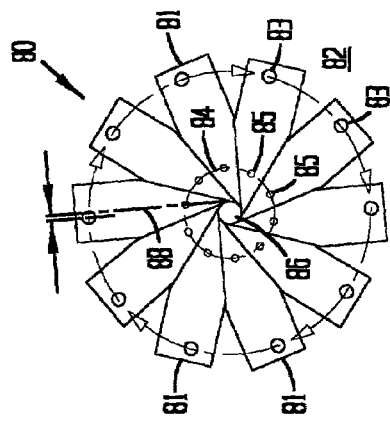

FIGS. 24A–C illustrates an alternative embodiment of the segmental, radial compression apparatus and the process of the present invention with proximally driven, off-centerline drive pins and distal, on-centerline pivot pins. The wedge 80 has ten segments 81. Proximal portions of the segments 81 are coupled to a driven (clockwise rotatable) plate 82 by drive pins 83, which are disposed off centerline 88 to the left (against the direction of drive plate 82 rotation). Distal portions of the segments 81 are pivotally coupled to a stationary hub 84 by pivot pins 85, which are disposed on centerline 88. The pivot pins 85 are permitted a slight amount of radial movement, with respect to the stationary hub 84 or to the segment 81, via elongated slotting, previously described. FIG. 24A illustrates a first state with a fully open aperture 86. The centerlines 88 of the segments 81 are not radially aligned, and the distal most points of the segments 81 are spaced from the wedge's central axis 87. FIG. 24B illustrates a second, intermediate state wherein, the hub 84 is traveling. The centerlines of the segments 81 are still not radially aligned. The distal most points of the segments are approaching the wedge's central axis 87. FIG. 24C illustrates a final state where the aperture is closed. The centerlines of the segments 81 are aligned and radiate from the central axis 87. The aperture is fully closed.

Figure 25A:
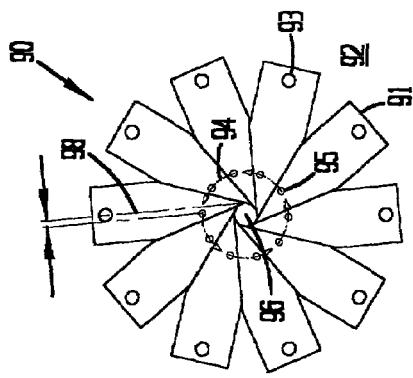
FIGS. 25A, B and C show a sequence of movement of a further alternative embodiment of the balloon pleating head, as the pleating aperture proceeds from an open to a closed state, the head embodiment having a distal offset and being distally driven.
Figure 25B:
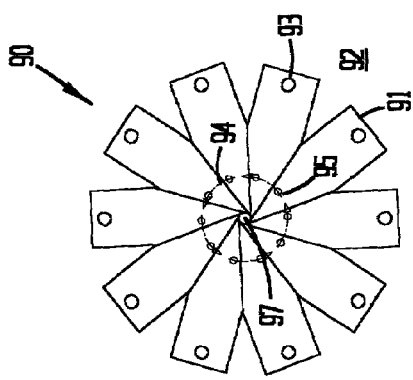
Figure 25C:
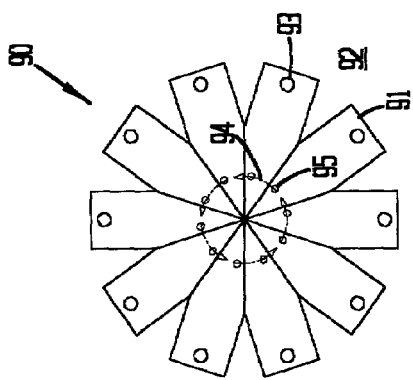

FIGS. 25A–C illustrates an alternative embodiment of the segmental, radial compression apparatus and the process of the present invention with distally driven, off-centerline drive pins and proximal, on-centerline pivot pins. The wedge 90 has ten segments 91. Proximal portions of the segments 91 are pivotally coupled to a stationary base 92 by pivot pins 93, which are disposed on centerline 98. The pivot pins 93 are permitted a slight amount of radial movement, with respect to the stationary base 92 or to the segment 91, via elongated slotting, previously described. Distal portions of the segments 91 are coupled to a driven (counter-clockwise rotatable) drive hub 94 by drive pins 95, which are disposed off centerline 98 to the left (towards the direction of drive hub 94 rotation). FIG. 25A illustrates a first state with a fully open aperture 96. The centerlines 98 of the segments 91 are not radially aligned, and the distal most points of the segments 91 are spaced from wedge's central axis. FIG. 25B illustrates a second, intermediate state wherein the hub 94 is traveling. The centerlines of the segments 91 are still not radially aligned. The distal most points of the segments are approaching wedge's central axis 89. FIG. 25C illustrates a final state, where the aperture is closed. The centerlines of the segments 91 are aligned and radiate from the central axis 89. The aperture is fully closed.

Figure 26A:
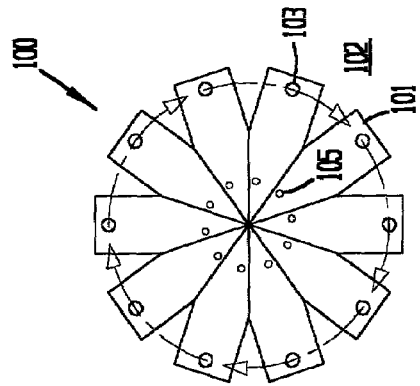
FIGS. 26A, B and C show a sequence of movement of a further alternative embodiment of the balloon pleating head, as the pleating aperture proceeds from an open to a closed state, the head embodiment having a distal offset and being proximally driven.
Figure 26B:
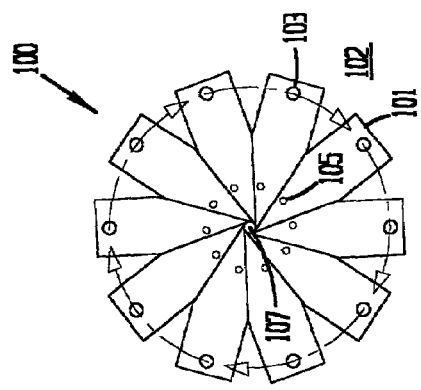
Figure 26C:
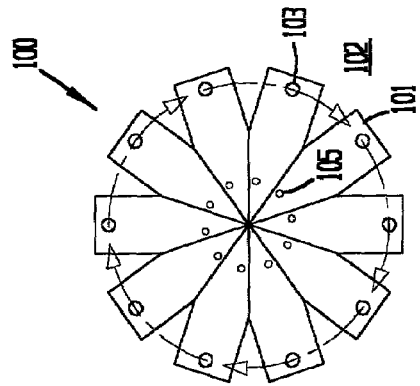

FIGS. 26A–C illustrates an alternative embodiment of the segmental, radial compression apparatus and the process of the present invention with proximally driven, on-centerline drive pins and distal, off-centerline pivot pins. The wedge 100 has ten segments 101. Proximal portions of the segments 101 are coupled to a driven (clockwise rotatable) plate 102 by drive pins 103, which are disposed on centerline 108. The drive pins 103 are permitted a slight amount of radial movement with respect to the driven plate 102 or to the segment 101, via elongated slotting, previously described. Distal portions of the segments 101 are pivotally coupled to a stationary hub 104 by pivot pins 105, which are disposed off centerline 108 to the left (against the direction of drive plate 102 rotation). FIG. 26A illustrates a first state with a fully open aperture 106. The centerlines 108 of the segments 101 are not radially aligned, and the distal most points of the segments 101 are spaced from the wedge's central axis. FIG. 26B illustrates a second, intermediate state wherein the hub 104 is traveling. The centerlines of the segments 101 are still not radially aligned. The distal most points of the segments are approaching the wedge's central axis 107. FIG. 26C illustrates a final state, where the aperture is closed. The centerlines of the segments 101 are aligned and radiate from the central axis 107. The aperture is fully closed.

Figure 27C:
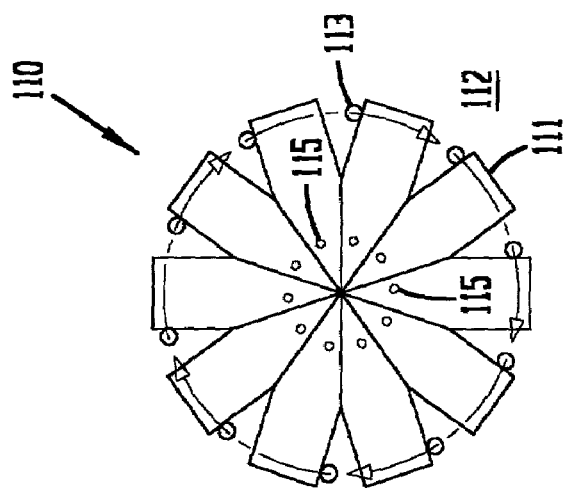
FIGS. 27A, B and C show a sequence of movement of a further alternative embodiment of the balloon pleating head, as the pleating aperture proceeds from an open to a closed state, the head embodiment having a distal offset and being proximally driven by a drive pin contacting an external surface of the segment.
Figure 27B:
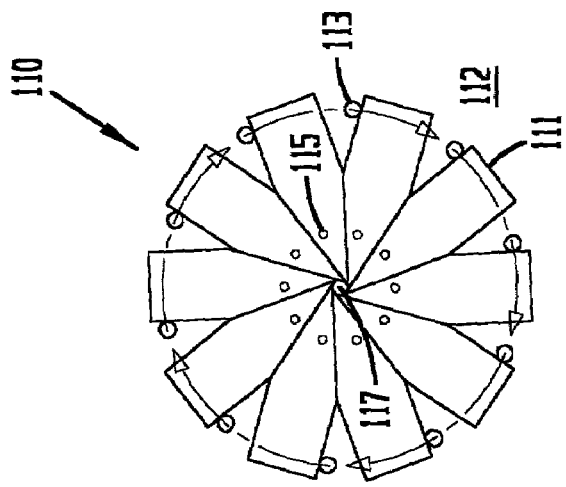
Figure 27A:
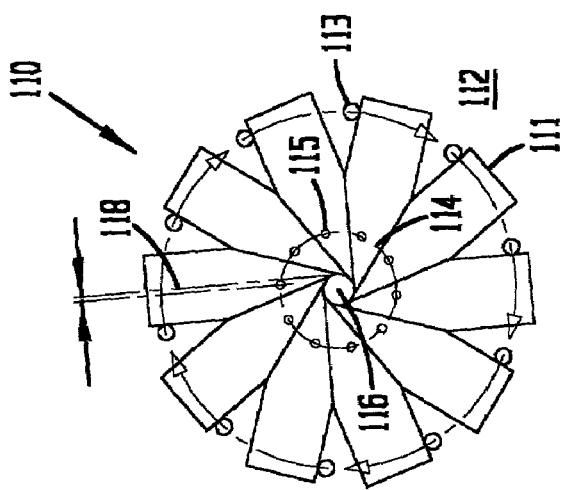

FIGS. 27A–C illustrates an alternative embodiment of the segmental, radial compression apparatus and the process of the present invention with proximally driven, off-centerline drive pins, which are disposed laterally to the side of the segments and distal, off-centerline pivot pins. The wedge 110 has ten segments 111. Proximal portions of the segments 111 are driven (clockwise rotatable), via plate 112 by drive pins 113, which are disposed off centerline 118. In this embodiment, in contrast to the embodiments shown in FIGS. 26A–C, the drive pins 113 are not captured by slots in the body portions of the segments 111. Instead, the drive pins 113 are disposed to the side of the segments 111 and contact the sides of the segments at a proximal region to drive them. Distal portions of the segments 111 are pivotally coupled to a stationary hub 114 by pivot pins 115, which are also disposed off centerline 118. FIG. 27A illustrates a first state with fully open aperture 116. The centerlines 118 of the segments 111 are not radially aligned, and the distal most points of the segments 111 are spaced from the wedge's central axis. FIG. 27B illustrates a second, intermediate state, wherein the hub 114 is traveling. The centerlines of the segments 111 are still not radially aligned. The distal most points of the segments are approaching the wedge's central axis 117. FIG. 27C illustrates a final state where the aperture is closed. The centerlines of the segments 111 are aligned and radiate from the central axis 117. The aperture is fully closed.

Figure 28C:
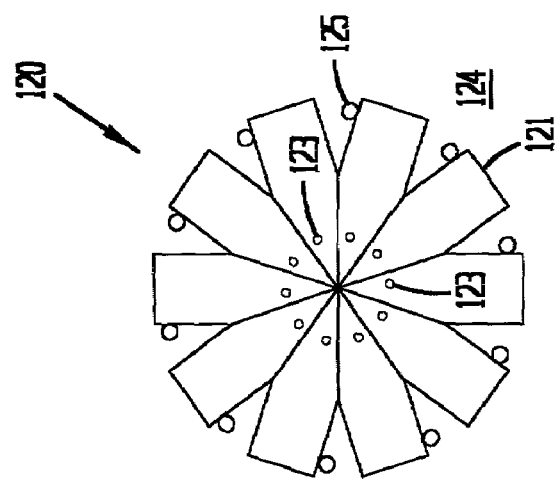
FIGS. 28A, B and C show a sequence of movement of a further alternative embodiment of the balloon pleating head, as the pleating aperture proceeds from an open to a closed state, the head embodiment having a distal offset and being distally driven by a drive pin, interior the segment, with pivot pins contacting an external surface of the segment.
Figure 28B:
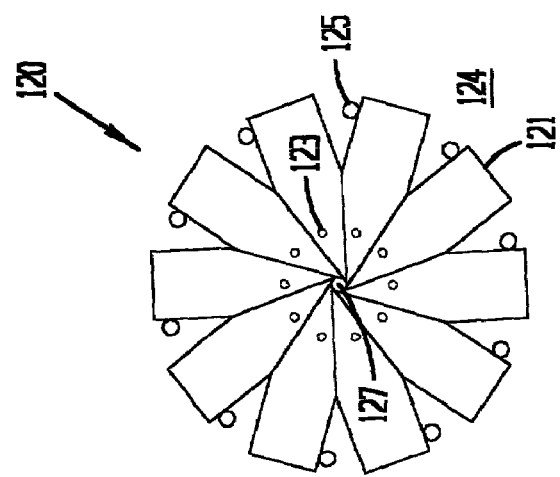
Figure 28A:
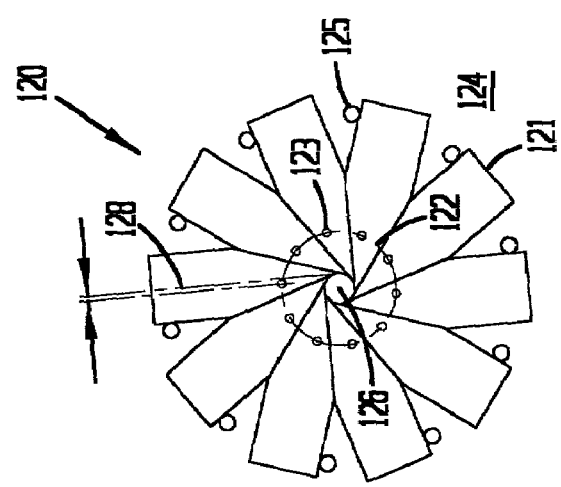

FIGS. 28A–C illustrates an alternative embodiment of the segmental, radial compression apparatus and the process of the present invention with distally driven, off-centerline drive pins, which are disposed laterally to the side of the segments and proximal, off-centerline pivot pins. The wedge 120 has ten segments 121. Distal portions of the segments 121 are coupled to a driven (counter-clockwise rotatable) hub 122 by drive pins 123, which are disposed off centerline 128. Proximal portions of the segments 121 are pivotally coupled to a stationary plate 124 by pivot pins 125, which are disposed off centerline 128. In this embodiment, in contrast to the embodiments shown in FIGS. 26A–C, the pivot pins 125 are not captured by slots in the body portions of the segments 121. Instead, the pivot pins 125 are disposed to the side of the segments 121 and contact the sides of the segments at a proximal region to pivot them. FIG. 28A illustrates a first state with fully open aperture 126. The centerlines 128 of the segments 121 are not radially aligned, and the distal most points of the segments 121 are spaced from the wedge's central axis. FIG. 28B illustrates a second, intermediate state wherein the hub 122 is traveling. The centerlines of the segments 121 are still not radially aligned. The distal most points of the segments are approaching the wedge's central axis 127. FIG. 28C illustrates a final state where the aperture is closed. The centerlines of the segments 121 are aligned and radiate from the central axis 127. The aperture is fully closed.

Figure 29A:
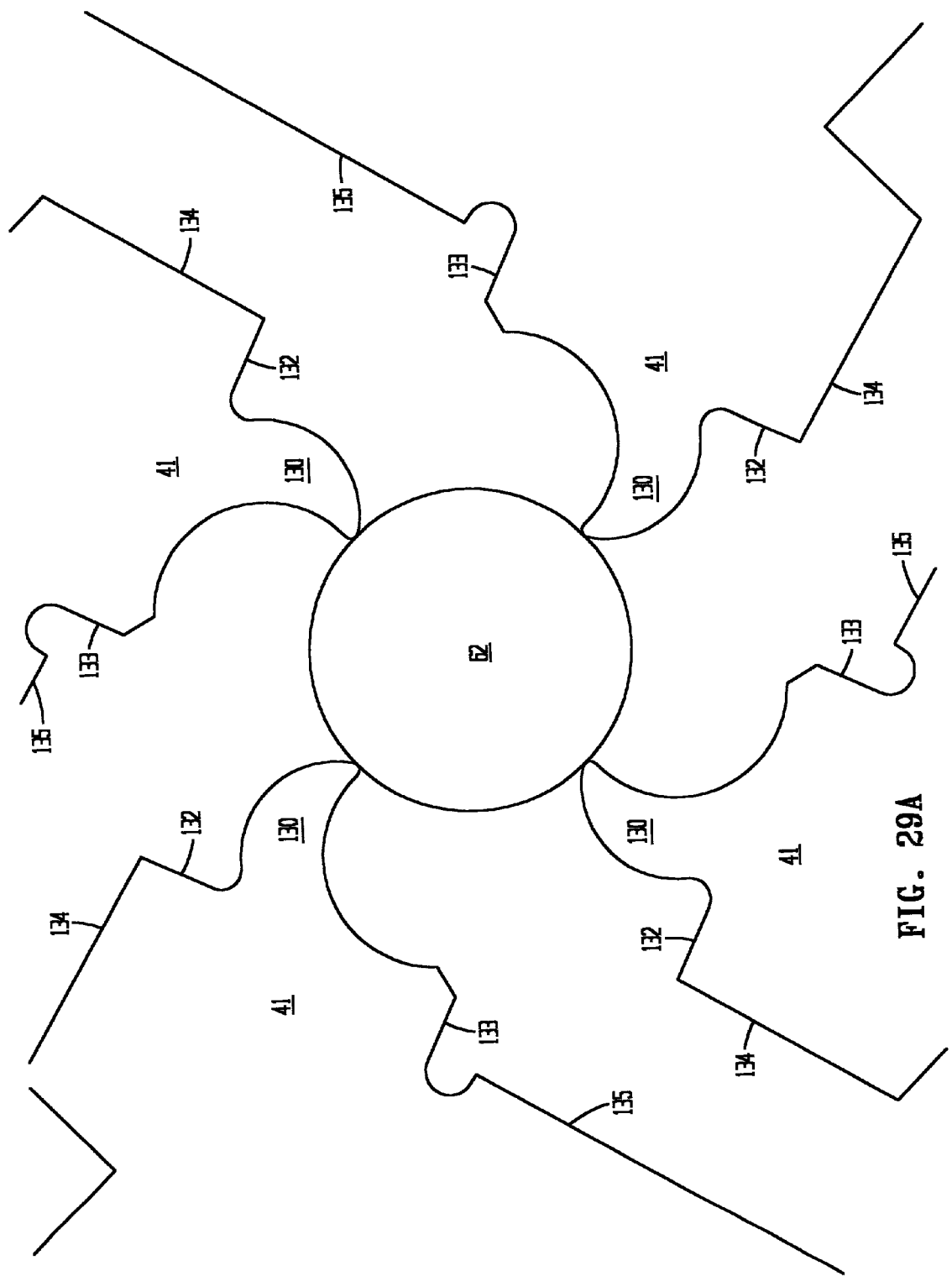
FIG. 29A is an enlarged cross sectional view of a pleating head in the open condition, with a balloon in the central pleating aperture.
Figure 29B:
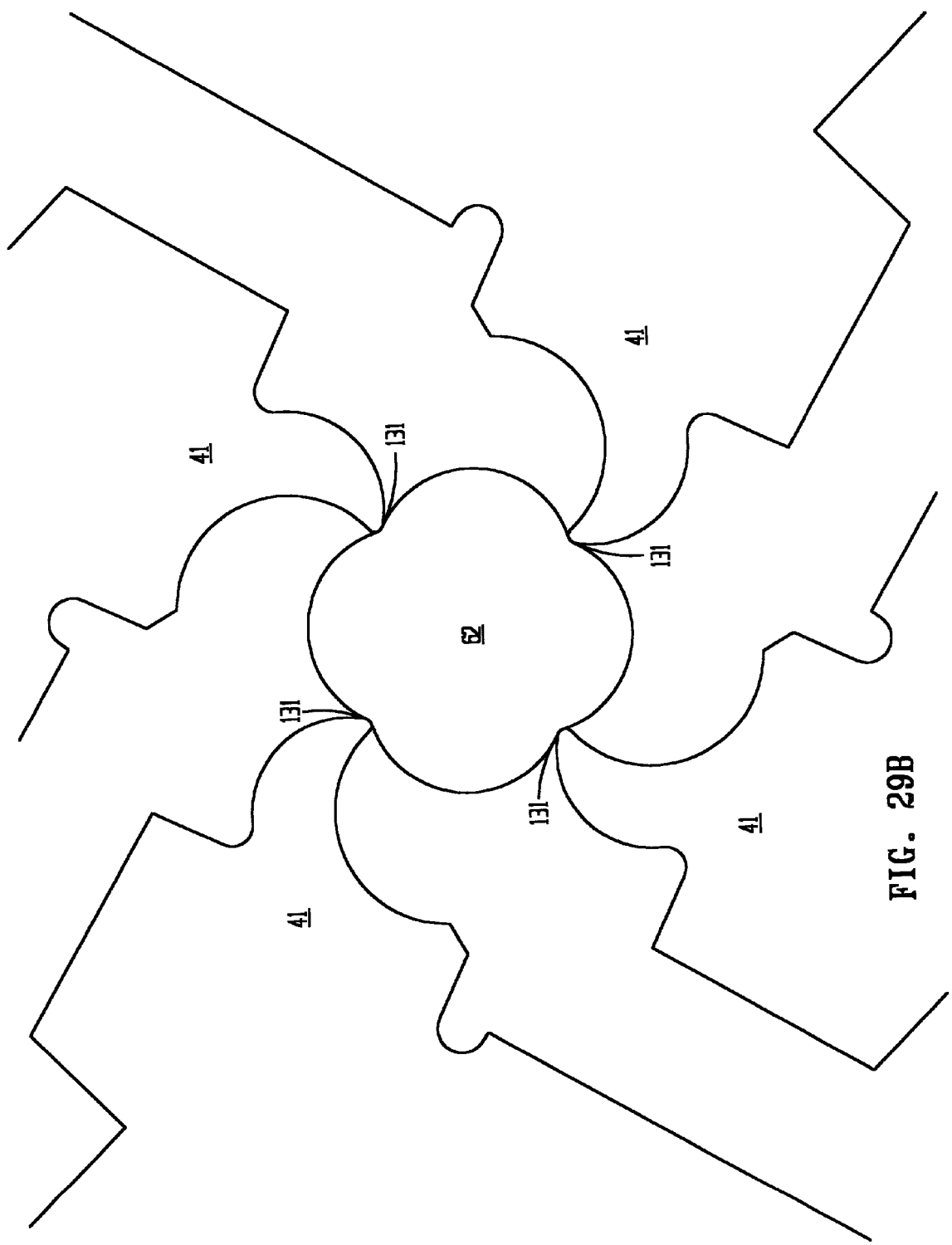
FIG. 29B is an enlarged cross sectional view of a pleating head in a partially closed condition, with a balloon in the central pleating aperture.
Figure 29C:
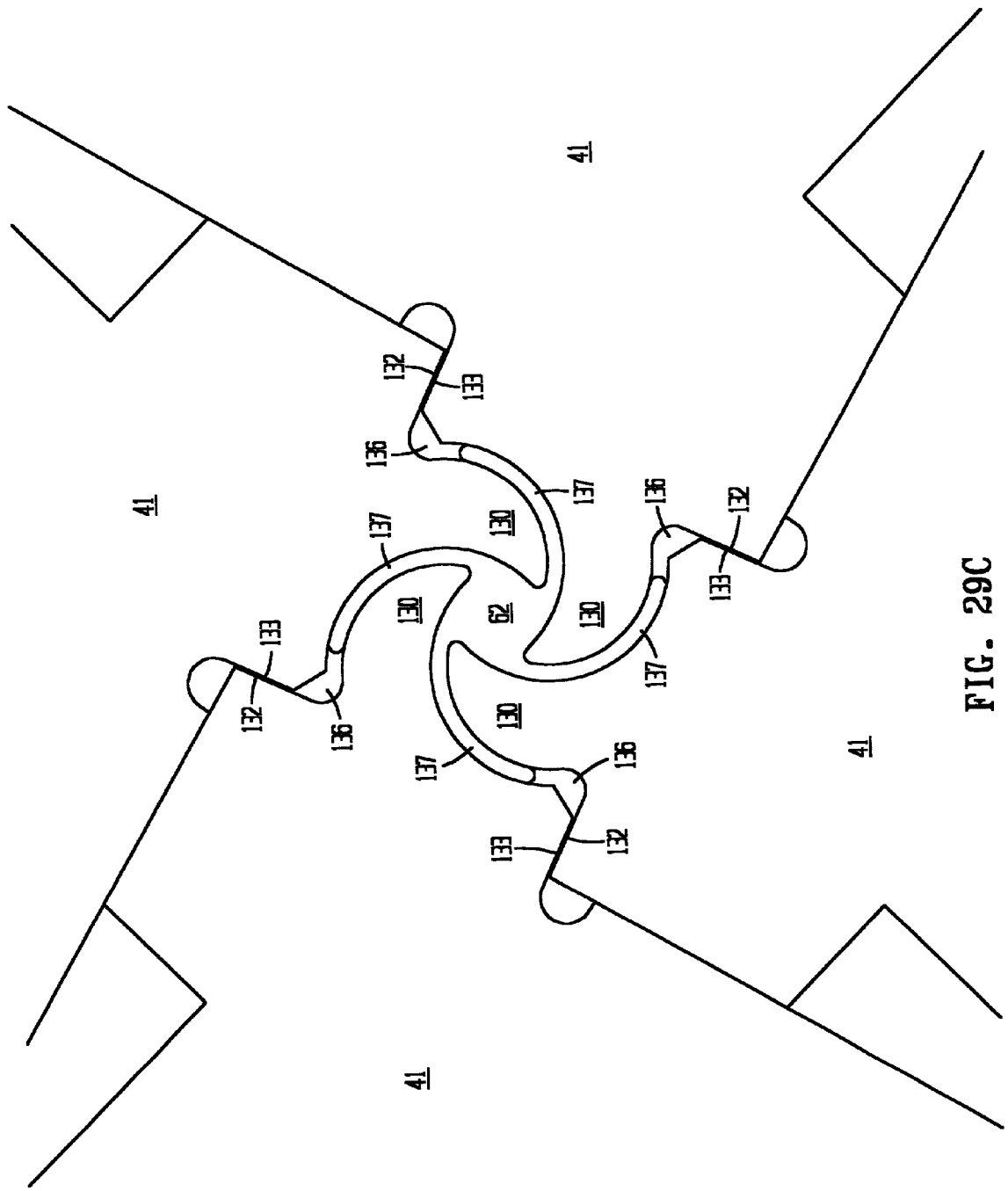
FIG. 29C is an enlarged cross sectional view of a pleating head in the closed condition, with a balloon in the central pleating aperture.

Referring now to FIGS. 29A–29C, an enlarged cross sectional view of a pleating head 11 having four segments 33, with a balloon in the central pleating aperture 62, is shown. Each segment distal end 41 is identical and has a curvilinear structure with a curved projecting end 130 having a point 131, which first contacts the balloon surface. The curved projecting end 130 extends the full length of the balloon, and the point 131 represents a thin linear surface that contacts the balloon along its complete length, or nearly so. Each distal end 41 also has stop surfaces 132 and 133 and contact surfaces 134, 135. As the hub 23 rotates, the drive pins 26 pivot the segments to move the distal ends 41 closer to the pleating head 11 center point. FIG. 29A depicts the condition where the point 131 of the curved projecting end 130 of each segment distal end 41 contacts the balloon surface. As rotation of the hub 23 continues, the point 131 of segment distal end 41 begins to pleat the balloon, as depicted in FIG. 29B. Continued rotation of the hub 23 brings the segment's distal ends 41 to a fully closed condition, depicted in FIG. 29C. With the pleating head 11 in the fully closed condition, the stop surface 132 of each segment 33 abuts the stop surface 133 on an adjacent segment 33 to prevent further movement of the distal ends 41, closer to the pleating head 11 center point. The contact surface 134 of each segment 33 tangentially approaches and meets a contact surface 135 of an adjacent segment 33. With the stop surface 132 of each segment 33 in abutment contact with the stop surface 133 of an adjacent segment 33, and the contact surfaces 134 of each segment 33 meeting a contact surface 135 of an adjacent segment 33, the curved projecting end 130 can move no nearer the center point, and pleating ceases. The stops 132, 133 are positioned so that each curved projecting end 130 of the segment distal end 41 only approaches an adjacent curved projecting end 130, leaving a curved channel 136 there between, as seen in FIG. 29C. This structural feature of the segment's distal end 41 pleats the balloon in a spiral pattern having, in this embodiment, four wings 137 all in a similar curved configuration, with the base 138 of each wing angled relative to the balloon core.

Figure 30B:
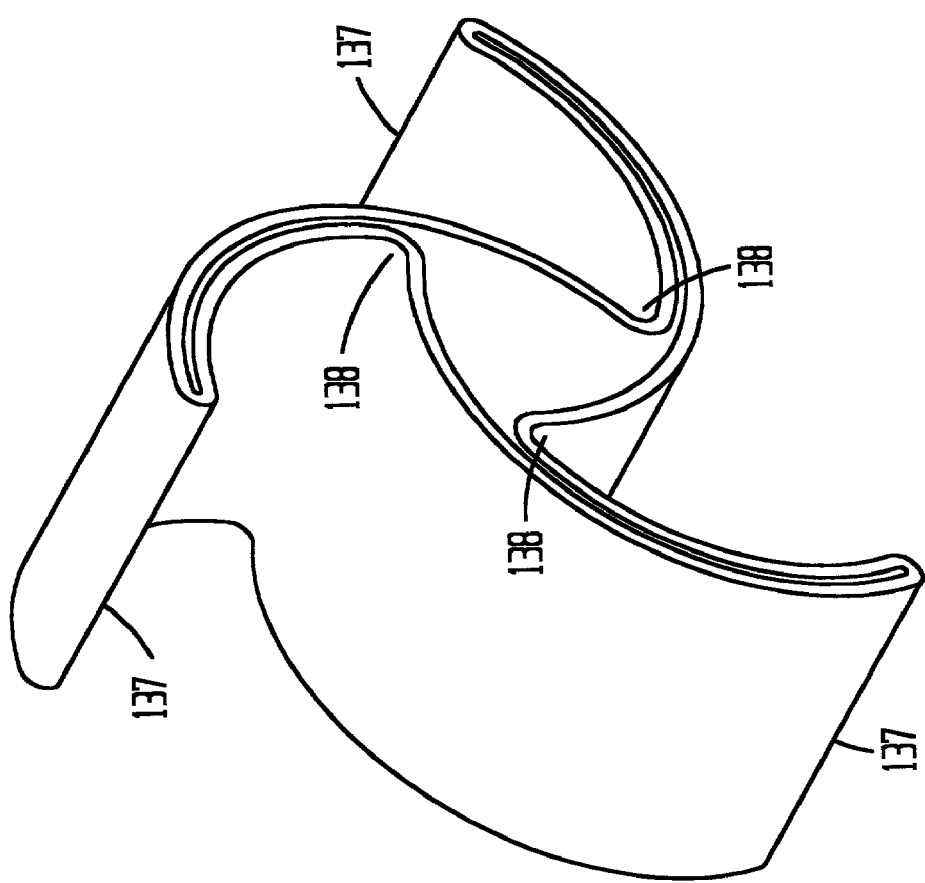
FIG. 30B is an enlarged sectional view of a portion of a pleated balloon, made with the pleating head of FIG. 30A.

An enlarged cross sectional view of a pleating head 11, having three segments 33 in a fully closed condition, is depicted in FIG. 30A. The central aperture with three spiral, curved channels 136 extending therefrom is readily apparent. A section of a spiral-pleated balloon made with the three segment pleating head 11 is shown in FIG. 30B. Each wing 137 of the pleated balloon is curved in the same direction and the base 138 of each wing is angled, in preparation for folding the spiral-pleated wings to a small volume.

Figure 31A:
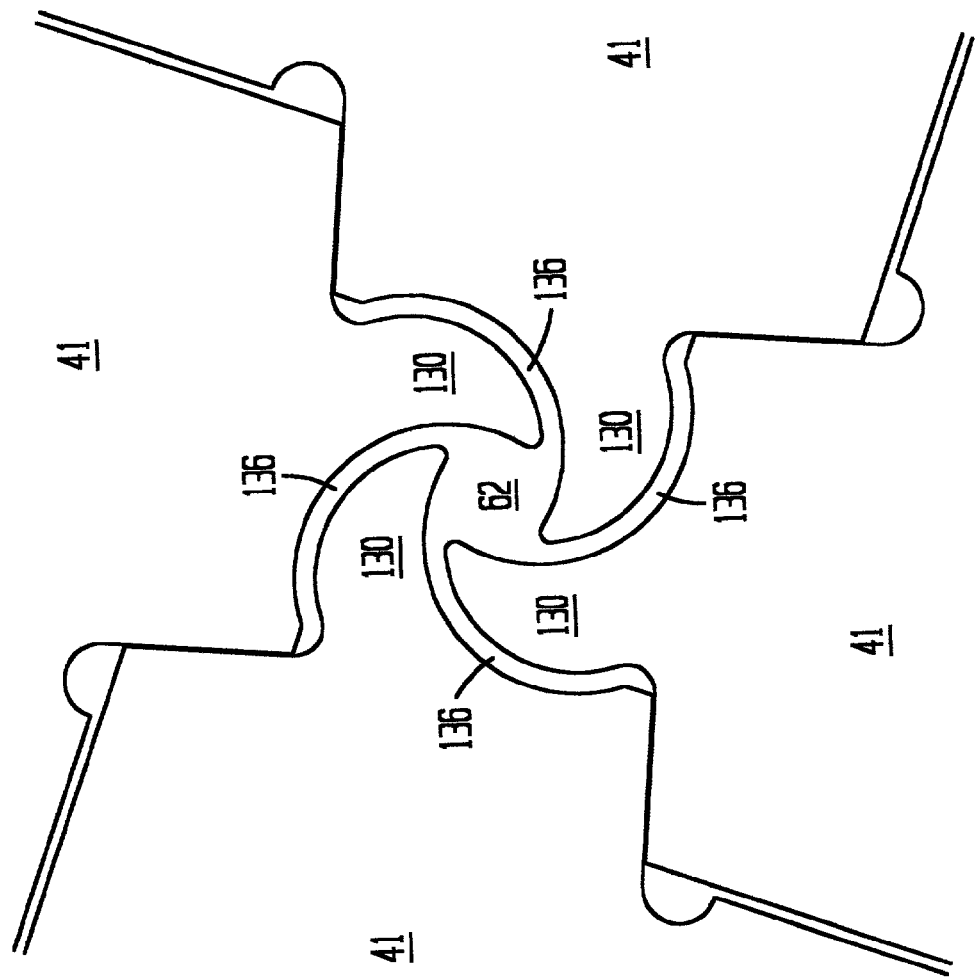
FIG. 31A is an enlarged cross sectional view of a pleating head, with four segments in the closed condition.
Figure 31B:
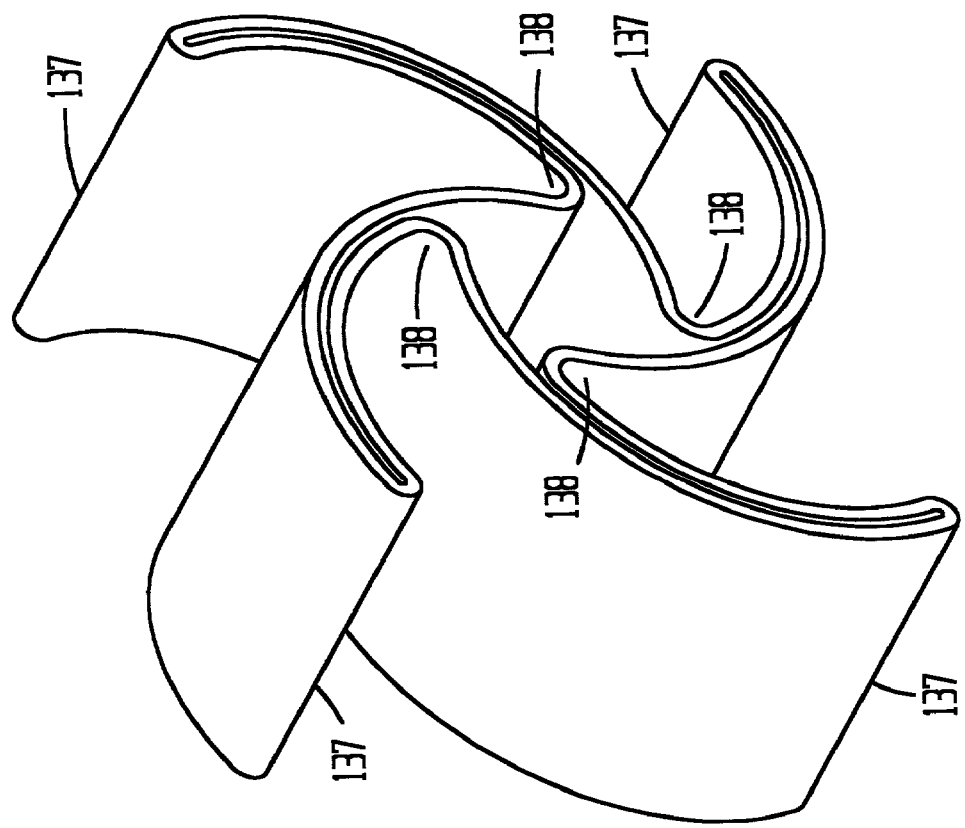
FIG. 31B is an enlarged sectional view of a portion of a pleated balloon, made with the pleating head of FIG. 31A.

An enlarged cross sectional view of a pleating head 11, having four segments 33 in a fully closed condition, is depicted in FIG. 31A. The central aperture with four spiral, curved channels 136 extending therefrom is readily apparent. A section of a spiral-pleated balloon made with the four segment pleating head 11 is shown in FIG. 31B. Each wing 137 of the pleated balloon is curved in the same direction and the base 138 of each wing is angled, in preparation for folding the spiral-pleated wings to a small volume.

Figure 32A:
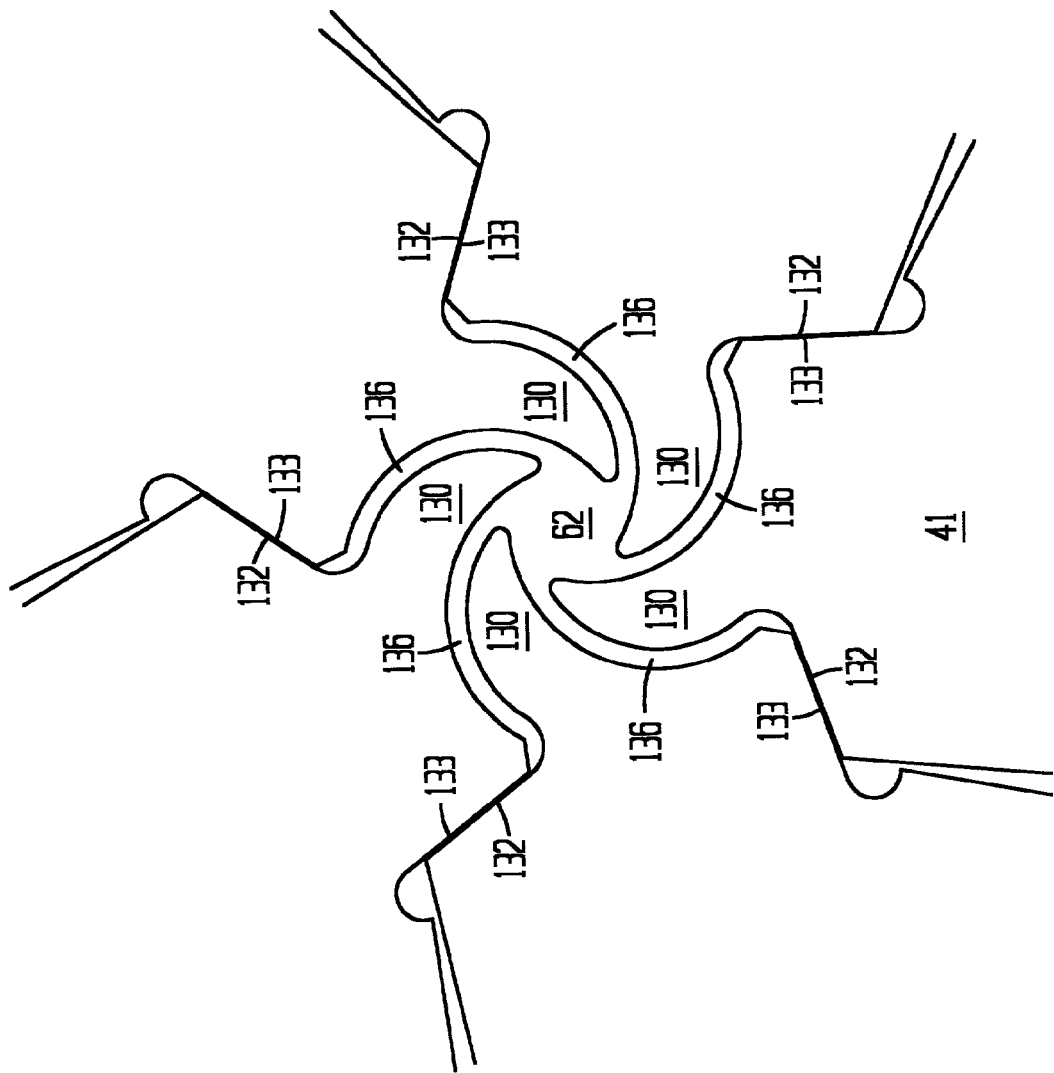
FIG. 32A is an enlarged cross sectional view of a pleating head, with five segments in the closed condition.
Figure 32B:
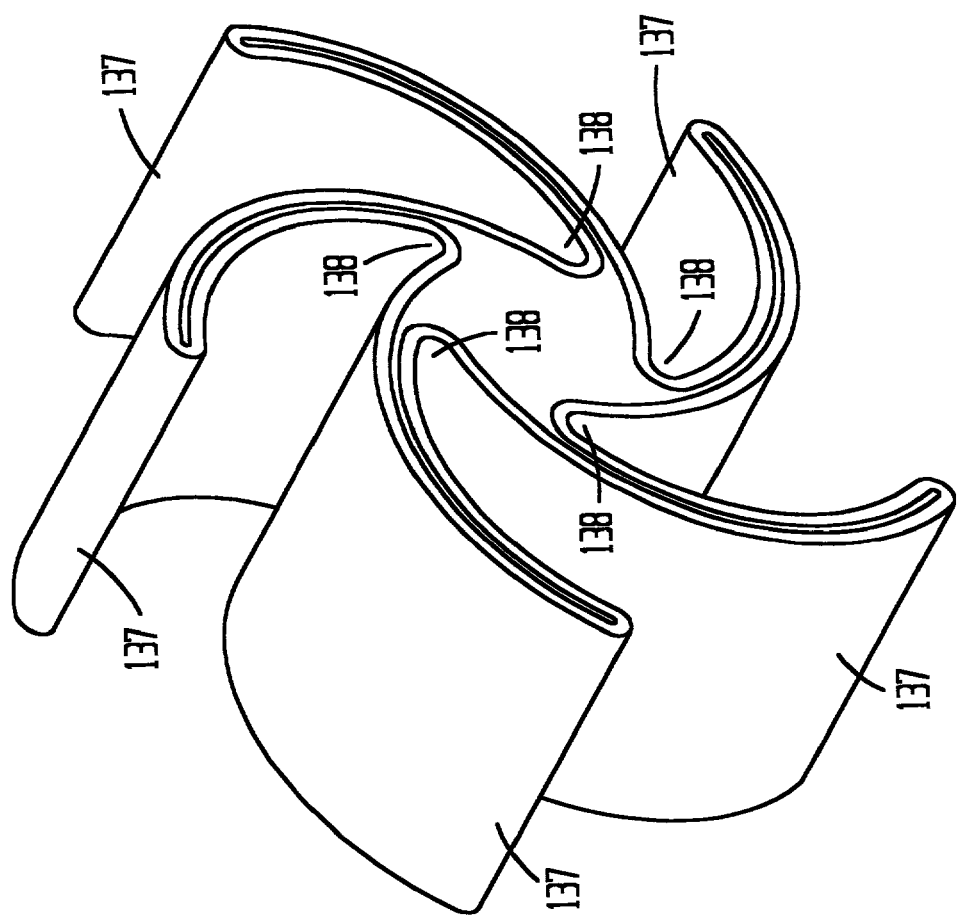
FIG. 32B is an enlarged sectional view of a portion of a pleated balloon, made with the pleating head of FIG. 32A.

An enlarged cross sectional view of a pleating head 11, having five segments 33 in a fully closed condition, is depicted in FIG. 32A. The central aperture with five spiral, curved channels 136 extending therefrom is readily apparent. A section of a spiral-pleated balloon made with the five segment pleating head 11 is shown in FIG. 32B. Each wing 137 of the pleated balloon is curved in the same direction, and the base 138 of each wing is angled, in preparation for folding the spiral-pleated wings to a small volume.

It is readily apparent that the number of spiral-pleated wings 137 that can be prepared for a balloon is limited only by the number of wedge segments 33 that can be assembled into a pleating head 11. Segments numbering three to sixteen are contemplated for providing a like number of spiral-pleated wings 137 for a balloon.

Figure 33:
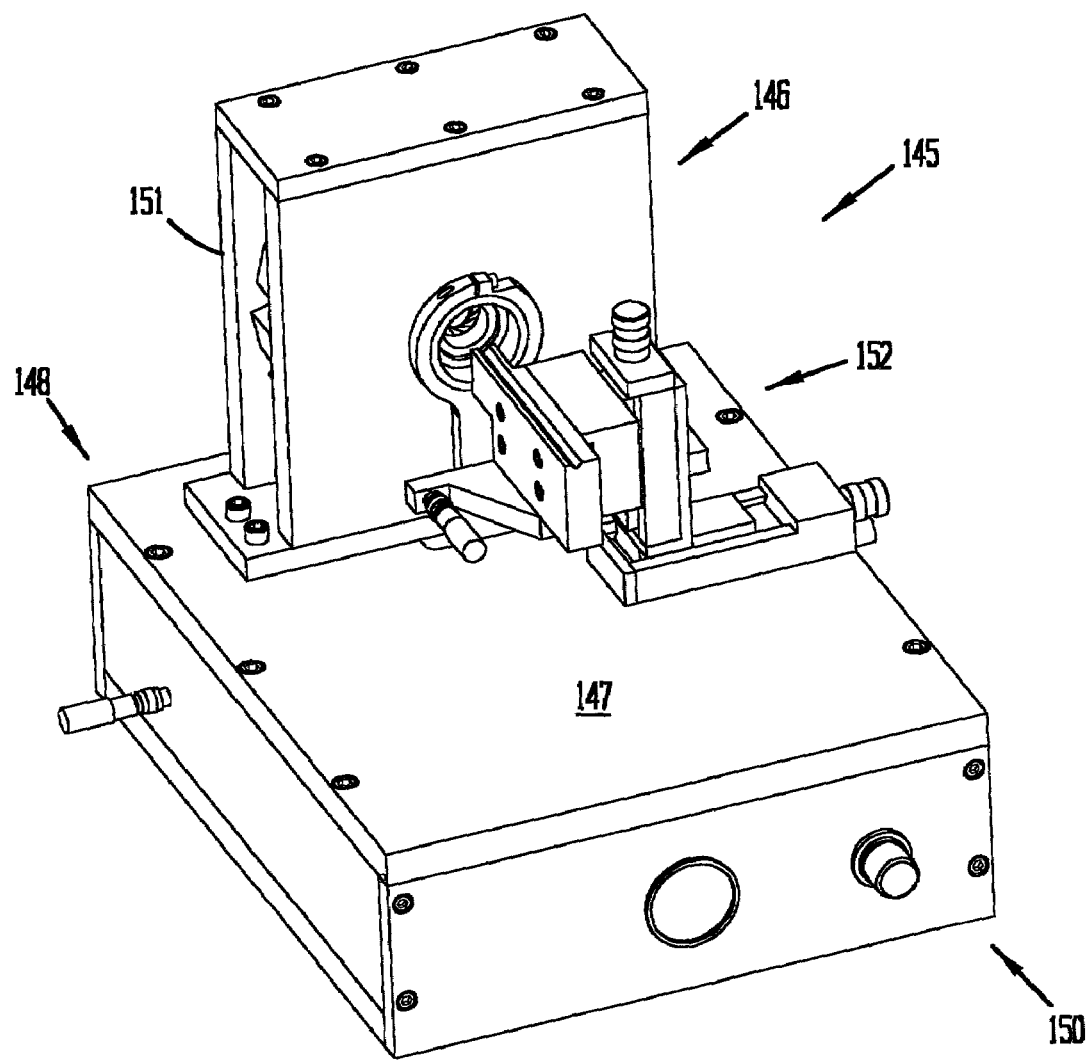
FIG. 33 is a perspective view of an alternative embodiment of the balloon folding system of the present invention, wherein the balloon pleating head is actuated by a pair of actuators located at the front and back of the head.
Figure 34:
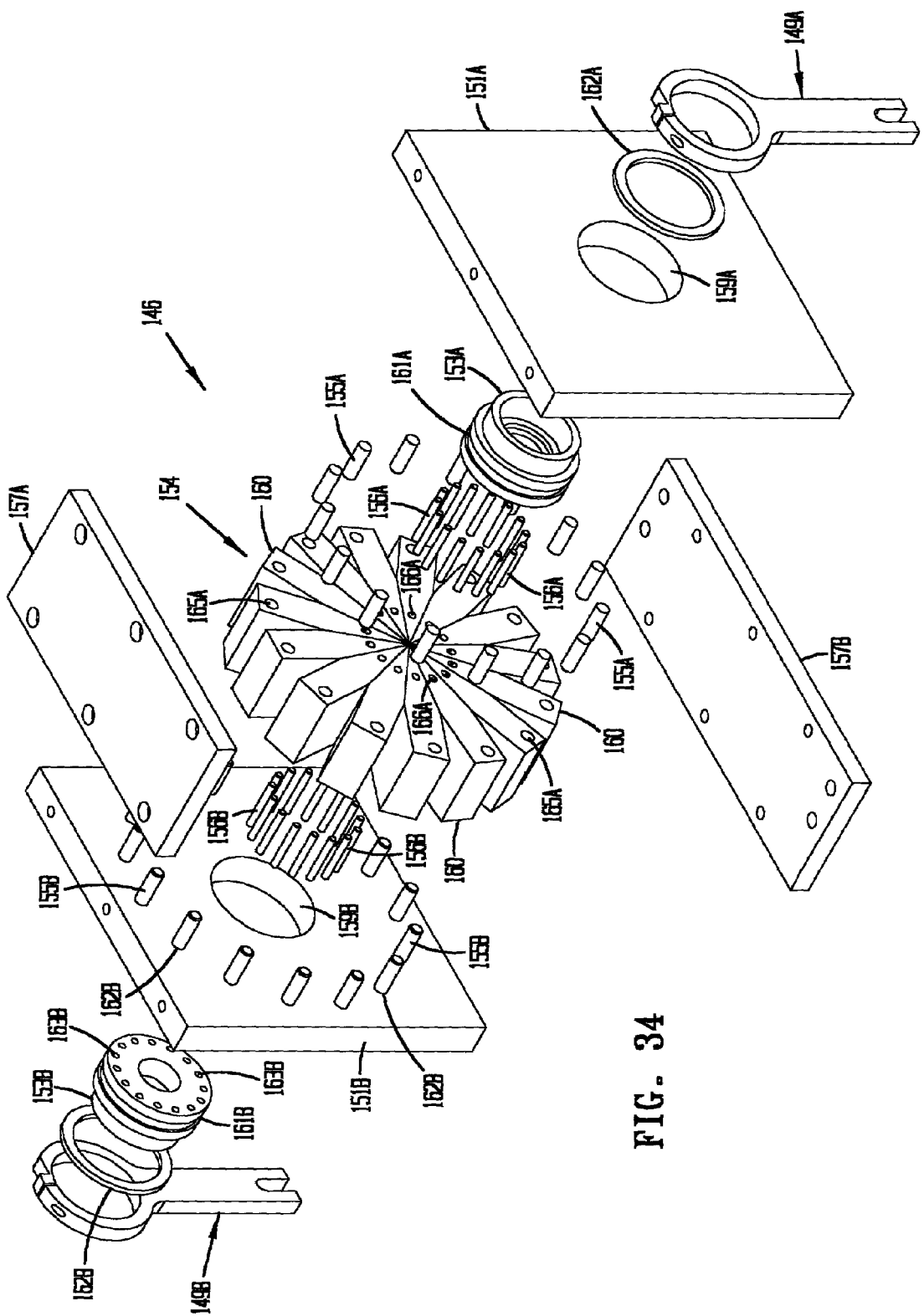
FIG. 34 is an exploded view of the pleating head, utilized in the balloon folding system of FIG. 33.
Figure 35:
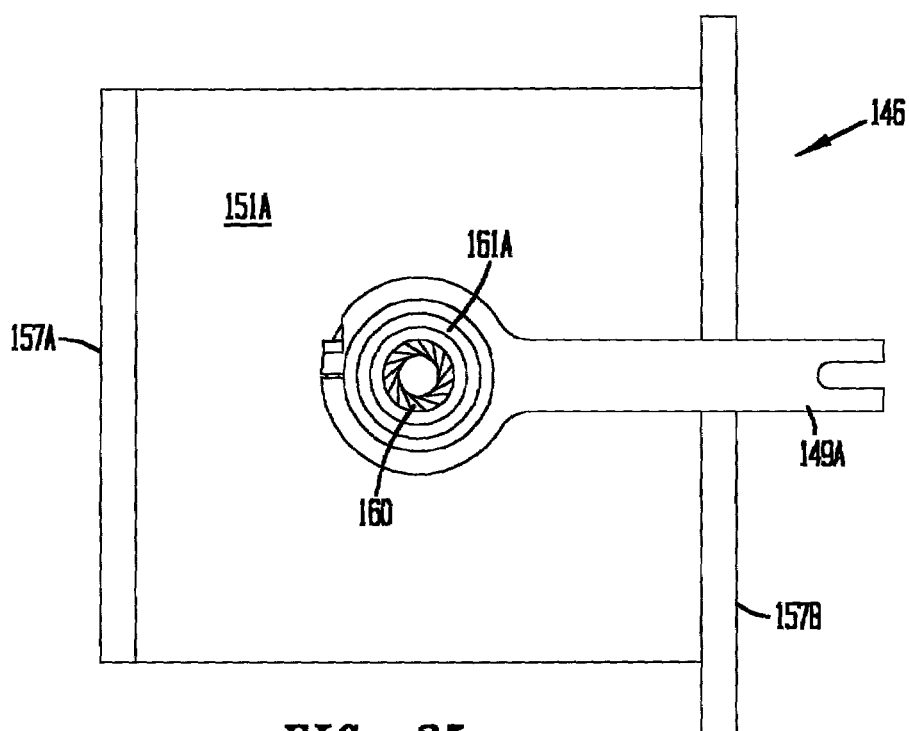
FIG. 35 is a front view of the balloon pleating head of the embodiment shown in FIGS. 33 and 34, with the pleating aperture in an open position and the arms in a corresponding position.
Figure 36:
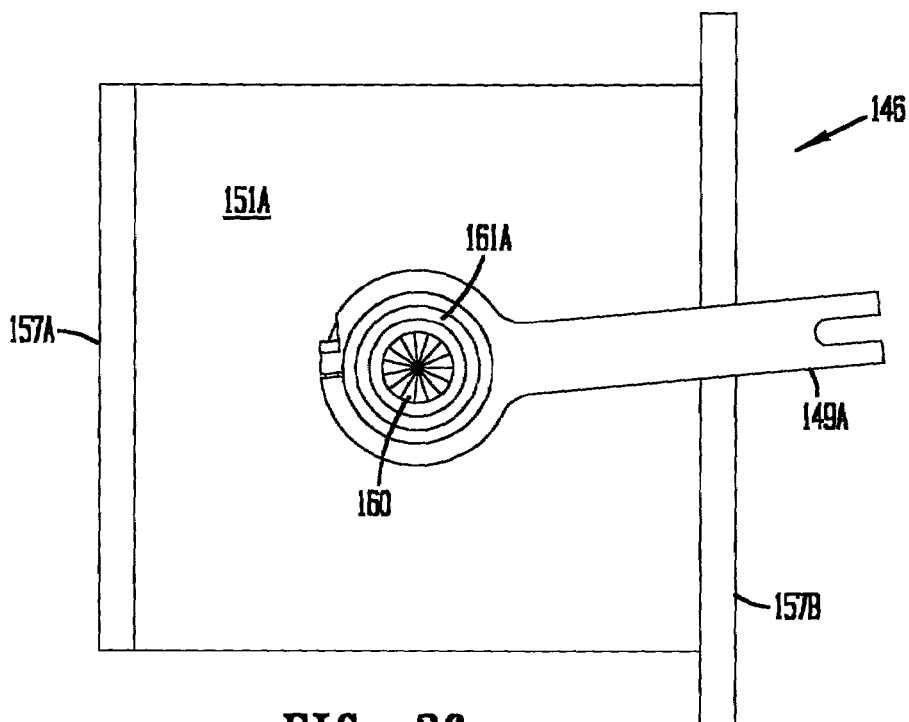
FIG. 36 is a front view of the balloon pleating of the dual arm embodiment, with the pleating aperture in a closed position and the arms in a corresponding position.
Figure 38:
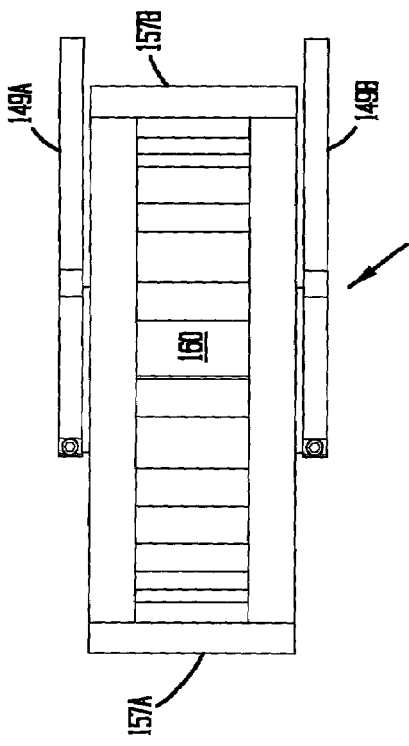
FIG. 38 is a bottom view of the balloon pleating head of the dual arm embodiment.
Figure 39:
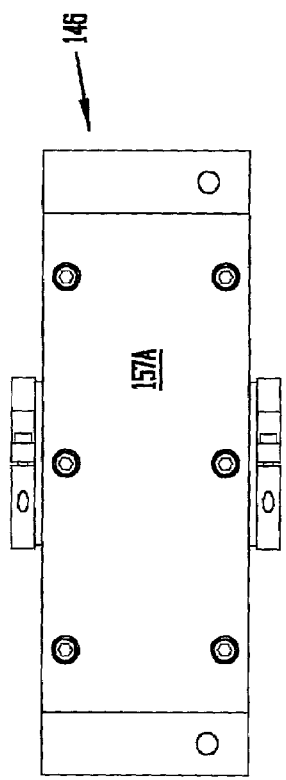
FIG. 39 is a side view of the balloon pleating head of the dual arm embodiment.
Figure 37:
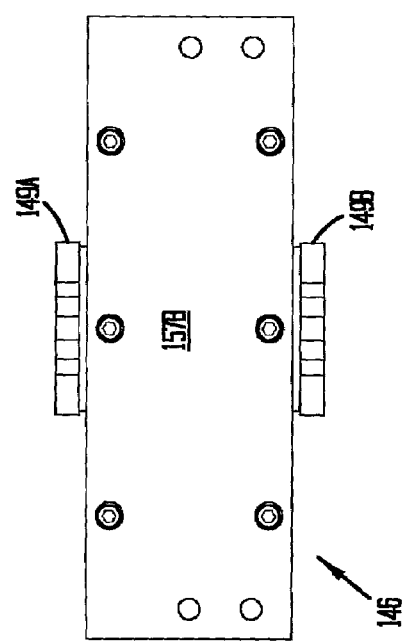
FIG. 37 is a top view of the balloon pleating head of the dual arm embodiment.
Figure 40:
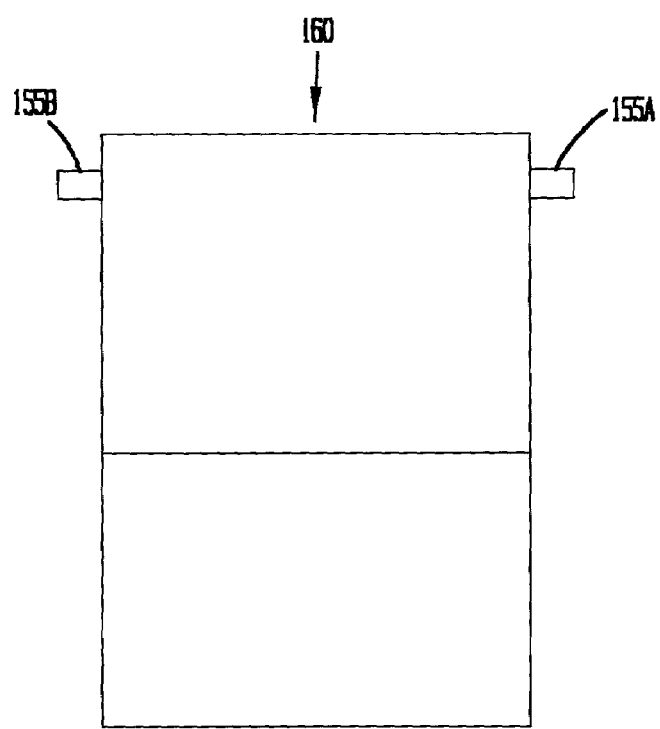
FIG. 40 shows a perspective view of an exemplary segment in the dual arm embodiment, having an increased length for longer balloons.
Figure 41:
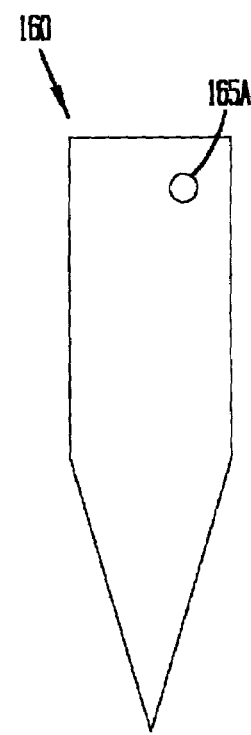
FIG. 41 shows a front view of the segment of FIG. 40.

The apparatus and methods of the present invention are useable with variable width articles ranging from 0.5 mm to 14148 mm, to accommodate both long and short balloons. To uniformly pleat a longer balloon, it may be desirable to apply a pleating force at both sides of a segment. Referring to FIGS. 33 and 34, an embodiment of the pleating system 145 for pleating relatively longer balloons and the like generally includes a pleating head 146, a base 147, and an actuator 148. The pleating head 146 is disposed on the base surface 147 and primary functions to accept and pleat balloons. The actuator 148 powers the pleating head 146. The actuator 148 preferably includes a drive mechanism, a linkage assembly communicatively connected to the drive mechanism, actuation arms 149A and B, which are communicatively connected to the linkage assembly and to the pleating head 146, and an actuation control system 150 communicatively connected to the drive mechanism. The actuator 148 may be hand and/or foot operable by an operator. The actuator 148 is preferably a pneumatic system, although other types of systems may be used. The system 145 further includes a balloon handling system 152. Additional systems, assemblies or mechanisms may be added to the basic system 145.

Referring also to FIGS. 35–41, the pleating head 146 shown has a relatively compact, preferably rectilinear, configuration. The pleating head 146 comprises, basically, a pair of base or housing plates 151A and B, a pair of drive hubs 153A and B, a radial compression wedge 154, two sets (each set including a plurality of pins, preferably 15) of pivot pins 155 A and B, two sets of drive pins 156 A and B, and a pair of separator plates 157A and B of a predetermined width, which couple the base plates 151A and B. The base plates 151 have a predetermined thickness with a central hub apertures 159A and B. The hubs 153 have an annular configuration with a flat face portion. The wedge 154 consists of a plurality of separate segments 160.

The hubs 153 are constructed of rigid, preferably metallic, material. The hubs 153 are preferably connected to respective annular roller bearings 161A and B. The hubs 153 are connected to respective actuator arms 149, preferably via respective thrust washers 162A and B. In this embodiment, the actuator arms 149 move in a counter-clockwise direction during actuation to perform a holding, compressing or pleating function. The base plates 151 are also constructed of a rigid, preferably metallic, material. The hubs 153 are rotatable with respect to the base plates 151. The wedge 154 has a roughly cylindrical configuration with a predetermined maximum depth and circumference, such that it is housed between the base plates 151. The pivot pins 155A and B mate with respective, aligned pivot slots 162A and B in base plates 151A and B, and further to respective, aligned pivot slots 165A and B in the front and rear faces of the segments 160 (at their proximal ends). The drive pins 156A and B mate with respect, aligned drive slots 163A and B in the drive hubs 153A and B, and further to respective, aligned drive slots 166A and B in the front and rear faces of the segments 160 (at their distal ends).

System 145, shown in FIGS. 33–39, functions in a similar manner to that of system 10, shown in FIGS. 8–10. In a normal mode, the actuation arms 149A and B are synchronized to move together to apply a uniform force along the entire edge of each of the relatively large wedges 160. Alternatively, the actuation arms 159A and B may be differentially actuated to provide a variable compression along the length of the wedges 160.

The pleating apparatus and method of the present invention is adaptable with thermal capability to operate at temperatures ranging between 37° C. and 300° C., by placing heater cartridges in the segments through its back. The balloon pleating devices 10 and 125 are adaptable to compensate for thermal expansion. Further, the apparatus and methods are adaptable with cryo capability to operate at temperature ranging between −200° C. and −37° C. Liquid nitrogen may be used to cool the segments or to cool the housing plates. Alternatively, the entire head may be placed in a cryo chamber.

Figure 42:
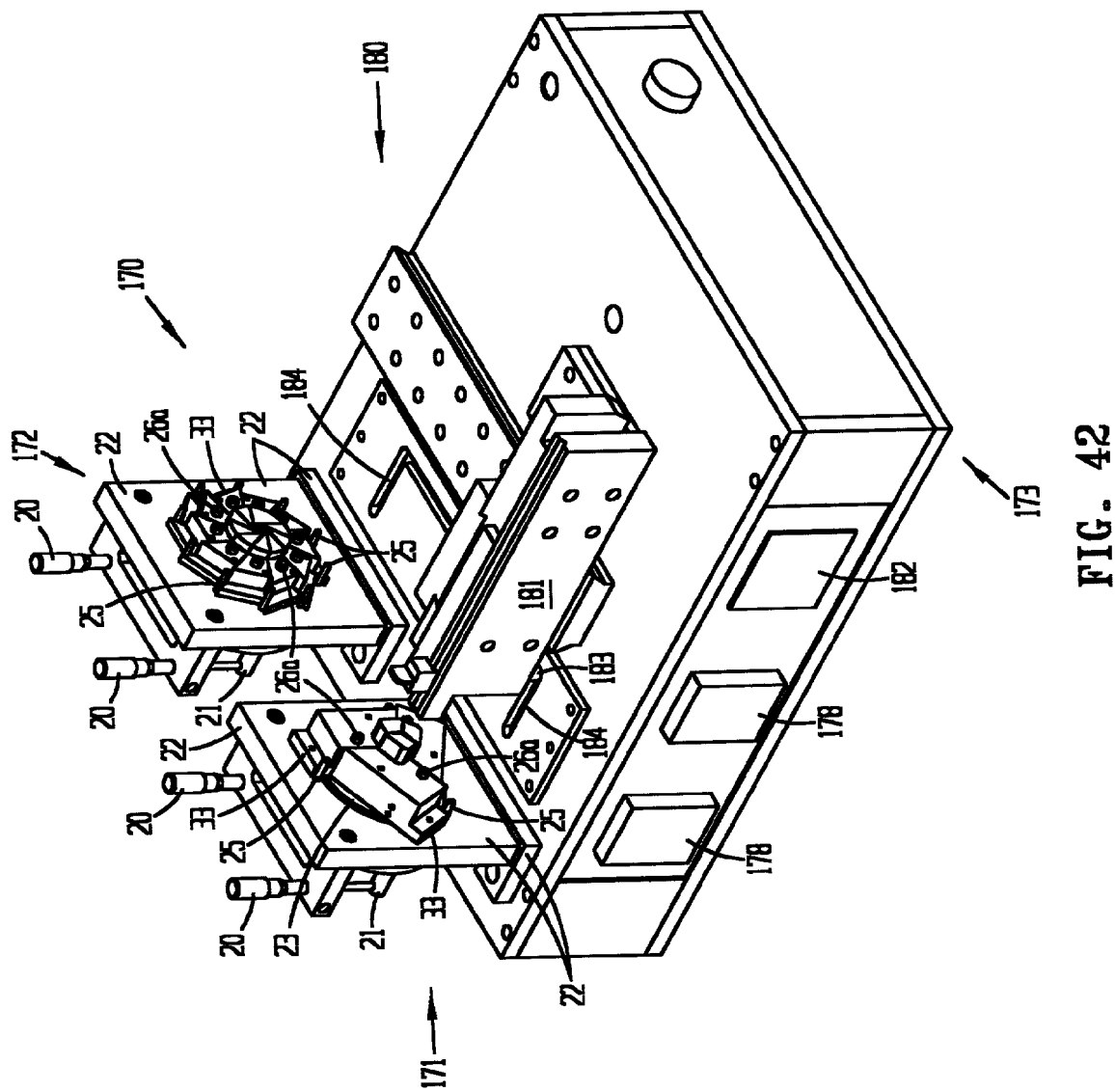
FIG. 42 is a perspective view of a balloon pleating and folding system.
Figure 43:
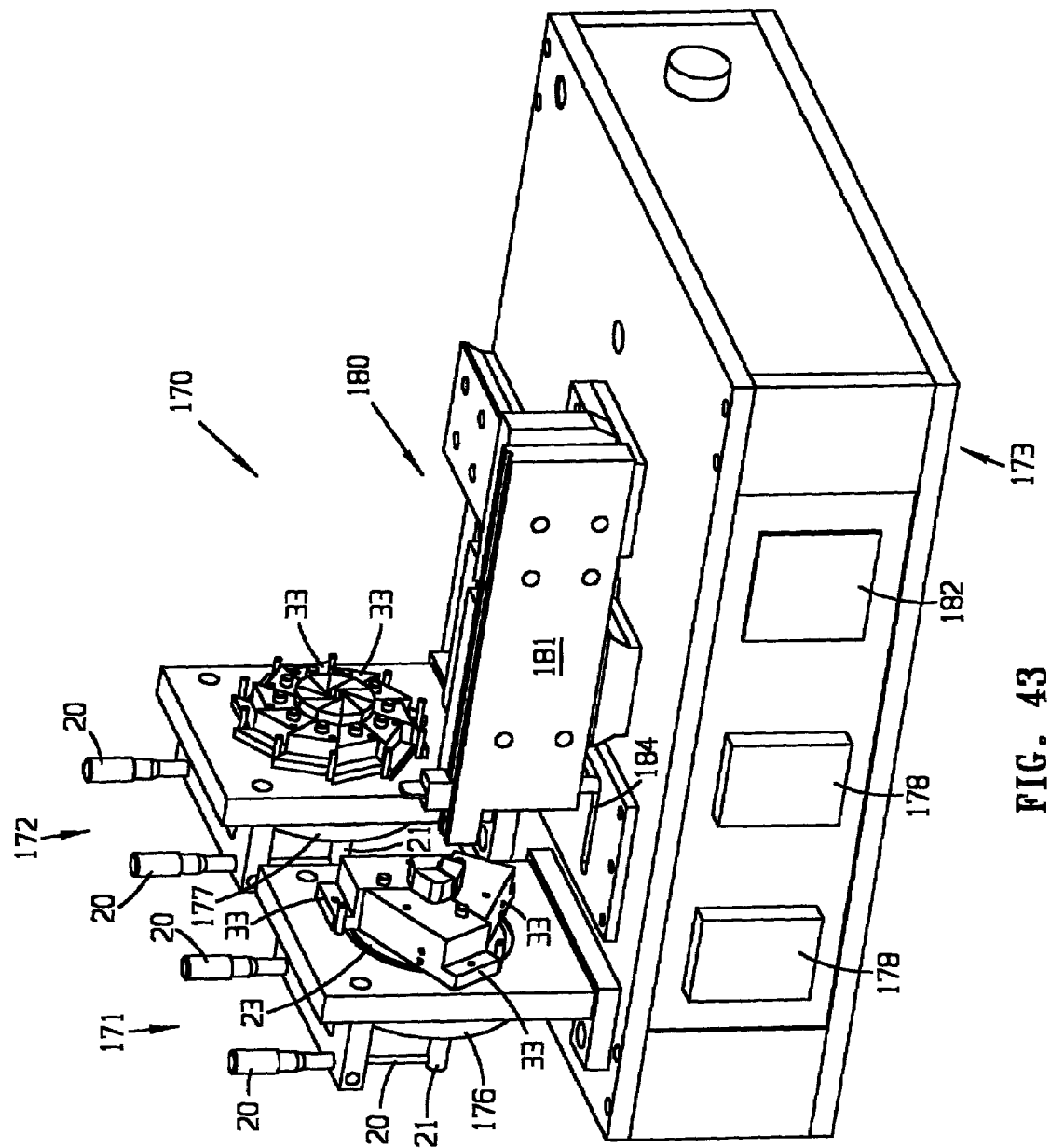
FIG. 43 is another perspective view of the balloon pleating and folding system of FIG. 42.

Referring now to FIGS. 42 and 43, a system 170 for pleating and folding a catheter balloon and the like is shown. The pleating and folding system 170 includes a pleating head assembly 171 and a folding head assembly 172, each disposed on a base unit 173. Preferably the head assemblies 171, 172 are coplanar, with central apertures at a common level for ease in consecutive operation. An actuator 174 contained within the base unit 173 selectively powers the pleating head assembly 171 and the folding head assembly 172 by a suitable drive mechanism 175 connected to each actuation arm 176 and 177 of the head assemblies 171, 172, respectively. The base unit 173 also includes an actuation control system 178 communicatively connected to the drive mechanism 175 for selectively actuating each head assembly. The actuator 174 is preferably a pneumatic system. Alternatively, hydraulic, mechanical, electrical, or electromechanical actuators may be used, consistent with the basic teachings of the invention. It is within the purview of the invention that the balloon pleating and folding system 170 may be disposed on an existing table, bench or other work surface.

The balloon handling system 180 includes a transport mechanism 181 for moving the support member 181 longitudinally toward each head assembly and laterally between the two head assemblies. For example, the support member 181 rides on a vertical shaft 183 that extend through a transport slot 184 in the base unit 173 to engage the transport mechanism 182. The slot 184 is U-shaped with leg portions aligned with each head assembly and a base portion for movement of the shaft 183 between the two leg portions. The support member 181 holding a balloon on a shaft moves toward the pleating head assembly 171 to insert the balloon therein for the pleating step. When pleating is finished, the support member 181 withdraws the pleated balloon from the pleating head assembly 171, moves to the folding head assembly 172, inserts the pleated balloon therein for folding, and finally withdraws the pleated and folded balloon on the shaft therefrom.

Figure 44:
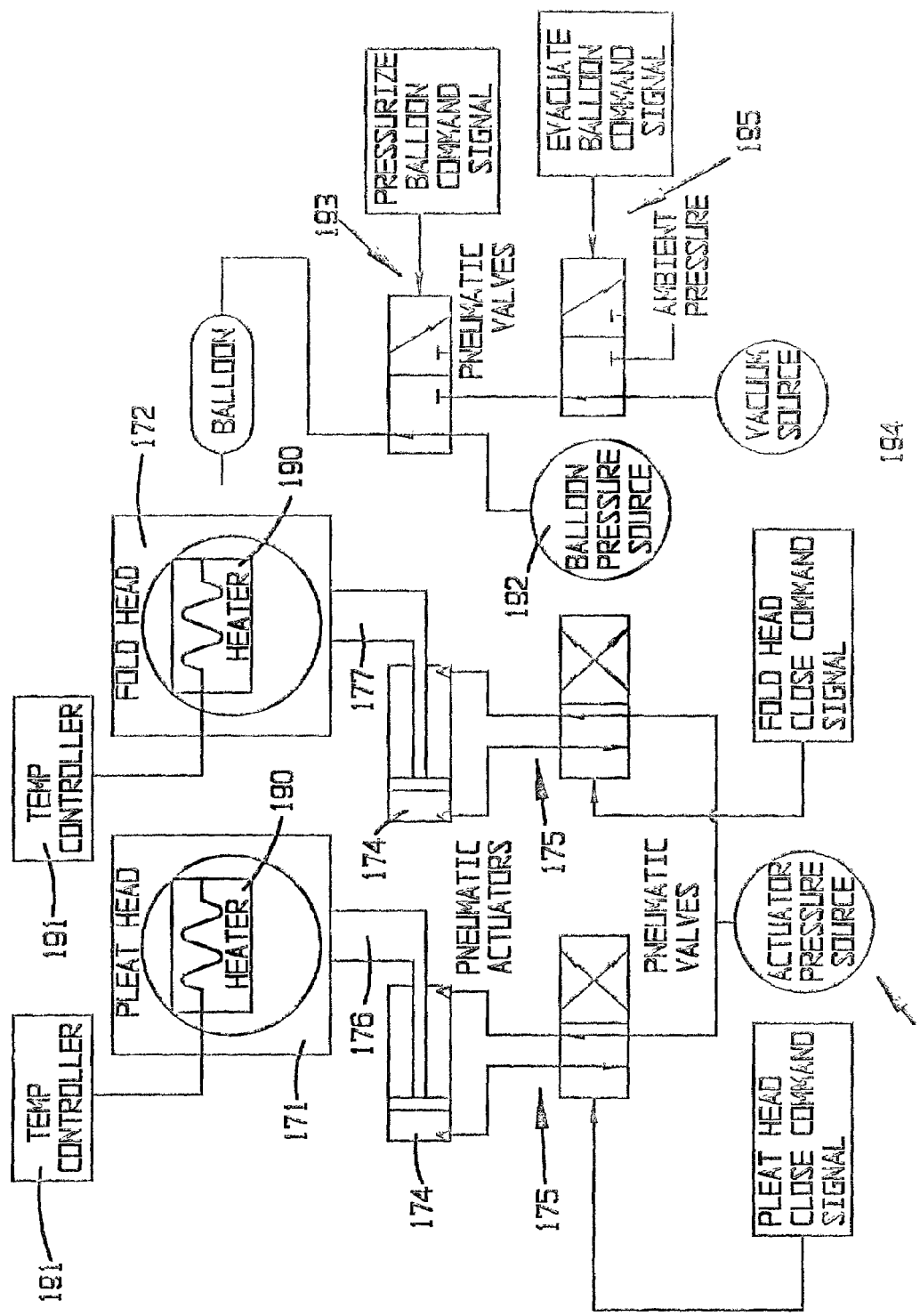
FIG. 44 is a functional schematic representation of the balloon pleating and folding system of FIG. 42.

FIG. 44 is a functional schematic representation of the balloon pleating and folding system 170. The pleating head assembly 171 and the folding head assembly 172 are actuated by pneumatic actuators 174 and controlled by an actuation control system 178. Each head assembly is fitted with individual heaters 190, connected to separate temperature controllers 191, for selectively heating each head assembly to set the pleated and folded configuration imparted on the balloon. Also included in the schematic is a balloon pressure source 192 and a pressure control 193 for lightly inflating the balloon prior to pleating, and a vacuum source 195 and vacuum control 196 for evacuating the pleated and/or folded balloon, following the pleating and/or folding steps. A typical sequence of steps involved in the balloon pleating and folding process is provided in FIG. 44, as well.

A balloon handling system 180 is also present on the base unit 173. The balloon handling system 180 includes a movable support member 181, adapted for holding a balloon on a shaft and inserting the balloon, consecutively, into the central aperture of the pleating head assembly 171 to spirally pleat the balloon, and then insert the spiral-pleated balloon into the central aperture of the folding head assembly 172, to fold the balloon spiral wings tightly around the balloon shaft.

Additional systems, assemblies or mechanisms may be added to the basic system outlined above. These additional systems include, but are not limited to, handling and alignment control and/or indication devices, pressure regulation and/or indication systems, calibration systems, control devices such as mechanical stops, vision assistance, laser micrometers, vacuum evacuation systems, heating and/or cooling systems, interchangeable pleating heads and folding heads, and pleating or folding dwell timers. Further, the pleating and folding system 170 may be controlled by an operator or automated.

The pleating head assembly 171 portion of the system is described in detail with respect to FIGS. 11a and 11b above. The folding head assembly 172 portion of the system operates in the same mode as the pleating head assembly 171, except that the distal end 41 of each wedge segment 33 is flat to produce a uniform radial compression on the spiral-pleated balloon to affect a tight folding of the balloon wings on the balloon support. The folding head assembly 172 is described in detail in copending U.S. Patent Application No. 60/210,319, filed Jun. 08, 2000, in the name of Tom Motsenbocker, and entitled, Stent Crimping Device. This application is hereby incorporated by reference as part of the specification.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim, if any, is expressed as a means or step for performing a specified function it, is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. An apparatus for pleating a balloon by segmental radial compression, comprising:

a. a pair of aligned, stationary base members separated a predetermined distance;

b. a pair of aligned rotatable drive hubs which are moveable in relation to the stationary base member and in synchronization with each other; and
c. a pleating head aligned with respect to the base members and the drive hubs, and including at least three segments;
  i. the segments each having a proximal end and an angled distal end with at least one angled side face terminating in an edge of a predetermined length, each segment having a centerline between the proximal and distal ends, each segment having a proximal point and a distal point, the distal point being disposed off the centerline and the proximal point being disposed off the centerline, and the proximal point being pivotally coupled by pins to the stationary base members and the distal point being pivotally coupled by pins to the rotatable hub members;
  ii. the segments being arranged so that the segment distal ends are disposed adjacent to and a predetermined distance away from a central point and defining a central aperture with a spiral-pleat dimension having at least three channels in communication with a central aperture, and that the segment centerlines extending therefrom toward the segment distal ends are oriented away from the central point; and
  iii. the segment distal ends moving closer to the central point upon rotation of the rotatable hub members in a predetermined direction, whereby the balloon is disposed around a shaft substrate, aligned in the central aperture and pleated around the shaft substrate upon rotation of the rotatable hub.

2. An system for pleating and folding a balloon by segmental radial compression, comprising:
A. a balloon pleating head device including:
  a. a stationary base member;
  b. a rotatable drive hub which is moveable in relation to the stationary base member; and
  c. a pleating head aligned with respect to the stationary base member and to the rotatable drive hub, and including at least three segments;
    i. the segments each having a proximal end and an angled distal end with at least one angled side face terminating in an edge of a predetermined length, each segment having a centerline between the proximal and distal ends, each segment having a proximal point and a distal point, the distal point being disposed off the centerline and the proximal point being disposed off the centerline, and the proximal point being pivotally coupled by pins to the stationary base member and the distal point being pivotally coupled by pins to the rotatable hub member;
    ii. the segments being arranged so that the segment distal ends are disposed adjacent to and a predetermined distance away from a central point and defining a central aperture with a spiral-pleat dimension having at least three channels in communication with a central aperture, and that the segment centerlines extending therefrom toward the segment distal ends are oriented away from the central point; and
    iii. the segment distal ends moving closer to the central point upon rotation of the rotatable hub member in a predetermined direction, whereby the balloon is disposed around a shaft substrate, aligned in the central aperture and pleated around the shaft substrate upon rotation of the rotatable hub; and
B. a pleated balloon folding device including;
  a. a stationary base member;
  b. a rotatable drive hub which is moveable in relation to the stationary base member; and
  c. a folding head aligned with respect to the stationary base member and to the rotatable drive hub, and including at least ten segments;
    i. the segments each having a proximal end and an angled distal end with at least one angled side face terminating in an edge of a predetermined length, each segment having a centerline between the proximal and distal ends, each segment having a proximal point and a distal point, the distal point being disposed off the centerline and the proximal point being disposed off the centerline, and the proximal point being pivotally coupled by pins to the stationary base member and the distal point being pivotally coupled by pins to the rotatable hub member;
    ii. the segments being arranged so that the segment distal ends are disposed adjacent to and a predetermined distance away from a central point and defining a central aperture with a cylindrical dimension, and that the segment centerlines extending therefrom toward the segment distal ends are oriented away from the central point; and
    iii. the segment distal ends moving closer to the central point upon rotation of the rotatable hub member in a predetermined direction, whereby the pleated balloon disposed around a shaft substrate, is aligned in the central aperture and folded around the shaft substrate upon rotation of the rotatable hub.

* * * * *